US011426311B2

(12) United States Patent
Wright et al.

(10) Patent No.: US 11,426,311 B2
(45) Date of Patent: *Aug. 30, 2022

(54) METHOD OF MAKING AN ABSORBENT COMPOSITE AND ABSORBENT ARTICLES EMPLOYING THE SAME

(71) Applicant: DSG TECHNOLOGY HOLDINGS LTD., Kwai Chung (HK)

(72) Inventors: Andrew C. Wright, Derbyshire (GB); Eugenio Varona, Marietta, GA (US)

(73) Assignee: DSG Technology Holdings Ltd., Kwai Chung (HK)

( * ) Notice: Subject to any disclaimer, the term of this patent is extended or adjusted under 35 U.S.C. 154(b) by 166 days.

This patent is subject to a terminal disclaimer.

(21) Appl. No.: 16/538,381

(22) Filed: Aug. 12, 2019

(65) Prior Publication Data

US 2020/0030163 A1 Jan. 30, 2020

Related U.S. Application Data

(63) Continuation of application No. 15/402,003, filed on Jan. 9, 2017, now Pat. No. 10,413,457, which is a
(Continued)

(51) Int. Cl.
*A61F 13/15* (2006.01)
*A61F 13/539* (2006.01)
(Continued)

(52) U.S. Cl.
CPC ...... *A61F 13/539* (2013.01); *A61F 13/15658* (2013.01); *A61F 13/536* (2013.01); *A61F 13/5323* (2013.01); *A61F 13/533* (2013.01)

(58) Field of Classification Search
CPC .............. A61F 13/539; A61F 13/15658; A61F 13/5323; A61F 13/536; A61F 13/534; A61F 13/533; A61F 2013/53908
See application file for complete search history.

(56) References Cited

U.S. PATENT DOCUMENTS 3,071,138 A 1/1963 Garcia
3,670,731 A 6/1972 Harmon
(Continued)

FOREIGN PATENT DOCUMENTS

CN 1177472 A 4/1998
CN 101426461 A 5/2009
(Continued)

OTHER PUBLICATIONS

2nd Office Action from Chinese Application No. 200780014162.9 filed Feb. 22, 2007, dated Aug. 29, 2012; 7 pages.
(Continued)

*Primary Examiner* — Jacqueline F Stephens
(74) *Attorney, Agent, or Firm* — Alberto Q. Amatong, Jr.; Amatong McCoy LLC

(57) ABSTRACT

Disclosed is a disposable absorbent article with a chassis body having a first end margin and a second end margin longitudinally spaced from the first end margins. The article further includes a topsheet, a backsheet, and an absorbent composite disposed between the topsheet and backsheet. The absorbent composite includes a first fabric, a second fabric, and absorbent particles disposed between the first and second fabric. The first fabric is intermittently attached to the second fabric to define a plurality of containers situated therebetween, each containing an aggregate of absorbent particles. The absorbent composite includes regions of such absorbent particles aggregates, including a primary region having containers of a first size and a secondary region having a plurality of containers of a second size.

25 Claims, 13 Drawing Sheets

Related U.S. Application Data continuation of application No. 14/026,927, filed on Sep. 13, 2013, now Pat. No. 9,566,198.

(60) Provisional application No. 61/801,620, filed on Mar. 15, 2013.

(51) Int. Cl.
*A61F 13/532* (2006.01)
*A61F 13/536* (2006.01)
*A61F 13/533* (2006.01)

(56) References Cited

U.S. PATENT DOCUMENTS

| | | |
|---|---|---|
| 3,780,399 A | 12/1973 | Morel |
| 3,814,100 A | 6/1974 | Nystrand et al. |
| 4,055,180 A | 10/1977 | Karami |
| 4,100,324 A | 7/1978 | Anderson et al. |
| 4,360,021 A | 11/1982 | Stima |
| 4,381,783 A * | 5/1983 | Elias ............ A61L 15/18 604/368 |
| 4,434,010 A | 2/1984 | Ash |
| 4,646,362 A | 3/1987 | Heran et al. |
| 4,670,011 A | 6/1987 | Mesek |
| 4,673,402 A | 6/1987 | Weisman et al. |
| 4,715,918 A | 12/1987 | Lang |
| 4,820,577 A | 4/1989 | Morman et al. |
| 4,960,477 A | 10/1990 | Mesek |
| 5,008,143 A | 4/1991 | Armanini |
| 5,037,412 A | 8/1991 | Tanzer et al. |
| 5,098,423 A | 3/1992 | Pieniak et al. |
| 5,122,407 A | 6/1992 | Yeo et al. |
| 5,149,335 A | 9/1992 | Kellenberger et al. |
| 5,281,207 A | 1/1994 | Chmielewski et al. |
| 5,294,478 A | 3/1994 | Wanek et al. |
| 5,336,552 A | 8/1994 | Strack et al. |
| 5,342,333 A | 8/1994 | Tanzer et al. |
| 5,350,370 A | 9/1994 | Jackson et al. |
| 5,364,380 A | 11/1994 | Tanzer et al. |
| 5,411,497 A | 5/1995 | Tanzer et al. |
| 5,425,725 A | 6/1995 | Tanzer et al. |
| 5,433,715 A | 7/1995 | Tanzer et al. |
| 5,436,066 A | 7/1995 | Chen |
| 5,458,592 A | 10/1995 | Abuto et al. |
| 5,482,761 A | 1/1996 | Palumbo et al. |
| 5,494,622 A | 2/1996 | Heath et al. |
| 5,505,718 A | 4/1996 | Roe et al. |
| H1565 H | 7/1996 | Brodof et al. |
| H1585 H | 8/1996 | Ahr |
| 5,549,589 A | 8/1996 | Horney et al. |
| 5,562,645 A | 10/1996 | Tanzer et al. |
| 5,562,646 A | 10/1996 | Goldman et al. |
| 5,567,744 A | 10/1996 | Nagata et al. |
| 5,591,149 A | 1/1997 | Cree et al. |
| 5,593,399 A | 1/1997 | Tanzer et al. |
| 5,599,335 A | 2/1997 | Goldman et al. |
| 5,601,542 A | 2/1997 | Melius et al. |
| 5,650,222 A | 7/1997 | DesMarais et al. |
| 5,653,702 A | 8/1997 | Brohammer et al. |
| 5,669,894 A | 9/1997 | Goldman et al. |
| 5,695,486 A | 12/1997 | Broughton et al. |
| 5,749,259 A | 5/1998 | Hamouda et al. |
| 5,763,331 A | 6/1998 | Demhartner |
| 5,782,819 A | 7/1998 | Tanzer et al. |
| 5,788,684 A | 8/1998 | Abuto et al. |
| 5,800,418 A | 9/1998 | Ahr |
| 5,821,179 A | 10/1998 | Masaki et al. |
| 5,853,403 A | 12/1998 | Tanzer et al. |
| 5,863,288 A | 1/1999 | Baker |
| 5,925,439 A * | 7/1999 | Haubach ............ A61F 13/5323 428/178 |
| 5,938,650 A | 8/1999 | Baer et al. |
| 5,941,862 A | 8/1999 | Haynes et al. |
| 5,944,706 A | 8/1999 | Palumbo et al. |
| 5,947,947 A | 9/1999 | Tanzer et al. |
| 5,994,614 A | 11/1999 | Wada et al. |
| 6,024,822 A | 2/2000 | Alper et al. |
| 6,046,377 A | 4/2000 | Huntoon et al. |
| 6,068,620 A | 5/2000 | Chmielewski |
| 6,071,549 A | 6/2000 | Hansen |
| 6,086,950 A | 7/2000 | Masaki et al. |
| 6,093,474 A | 7/2000 | Sironi |
| 6,129,720 A | 10/2000 | Blenke et al. |
| 6,140,550 A | 10/2000 | Beihoffer et al. |
| 6,152,906 A | 11/2000 | Faulks et al. |
| 6,162,959 A | 12/2000 | O'Connor |
| 6,177,607 B1 | 1/2001 | Blaney et al. |
| 6,238,379 B1 | 5/2001 | Keuhn et al. |
| H1969 H | 6/2001 | Fell et al. |
| 6,241,713 B1 | 6/2001 | Gross et al. |
| 6,245,693 B1 | 6/2001 | Gagliardi et al. |
| 6,258,076 B1 | 7/2001 | Glaug et al. |
| H1978 H | 8/2001 | Freiburger et al. |
| 6,290,686 B1 | 9/2001 | Tanzer |
| 6,329,565 B1 | 12/2001 | Dutkiewicz et al. |
| 6,368,990 B1 | 4/2002 | Jennergren et al. |
| 6,392,116 B1 | 5/2002 | Beihoffer et al. |
| 6,420,626 B1 | 7/2002 | Erspamer et al. |
| 6,429,350 B1 | 8/2002 | Tanzer et al. |
| 6,448,464 B1 | 9/2002 | Akin et al. |
| 6,458,877 B1 | 10/2002 | Ahmed et al. |
| 6,491,677 B1 | 12/2002 | Glaug et al. |
| 6,500,251 B1 | 12/2002 | Andes et al. |
| 6,534,572 B1 | 3/2003 | Ahmed et al. |
| 6,548,732 B2 | 4/2003 | Erdman et al. |
| 6,569,137 B2 | 5/2003 | Suzuki et al. |
| 6,570,056 B1 | 5/2003 | Tanzer et al. |
| 6,592,960 B1 | 7/2003 | Suzuki et al. |
| 6,610,900 B1 | 8/2003 | Tanzer |
| 6,632,209 B1 | 10/2003 | Chmielewski |
| 6,645,407 B2 | 11/2003 | Kellenberger et al. |
| 6,677,498 B2 | 1/2004 | Chen et al. |
| 6,680,423 B1 | 1/2004 | Tanzer |
| 6,689,205 B1 | 2/2004 | Brückner et al. |
| 6,689,934 B2 | 2/2004 | Dodge et al. |
| 6,700,035 B2 | 3/2004 | Yoshimasa |
| 6,702,800 B1 | 3/2004 | Vukos et al. |
| 6,730,069 B2 | 5/2004 | Tanzer et al. |
| 6,790,798 B1 | 9/2004 | Suzuki et al. |
| 6,797,360 B2 | 9/2004 | Varena |
| 6,849,672 B2 | 2/2005 | Mehawej et al. |
| 6,875,264 B2 | 4/2005 | Zimmermann et al. |
| 6,878,433 B2 | 4/2005 | Curro et al. |
| 6,899,776 B2 | 5/2005 | Bahlmann et al. |
| 6,965,058 B1 | 11/2005 | Raidel et al. |
| 6,972,011 B2 | 12/2005 | Maeda et al. |
| 7,321,007 B2 | 1/2008 | Gagliardi et al. |
| 7,699,825 B2 | 4/2010 | Nakagawa et al. |
| 7,722,590 B2 | 5/2010 | Tsuji et al. |
| 7,744,576 B2 | 6/2010 | Busam et al. |
| 7,750,203 B2 | 7/2010 | Becker et al. |
| 7,759,540 B2 | 7/2010 | Litvay et al. |
| 7,767,878 B2 | 8/2010 | Suzuki |
| 7,838,721 B2 | 11/2010 | Chen |
| 7,838,722 B2 | 11/2010 | Blessing et al. |
| 7,847,145 B2 | 12/2010 | Kurita et al. |
| 7,872,168 B2 | 1/2011 | Sawyer et al. |
| 7,994,233 B2 | 8/2011 | Mehawej et al. |
| 7,994,384 B2 | 8/2011 | Qin et al. |
| 8,148,598 B2 | 4/2012 | Tsang et al. |
| 8,163,124 B2 | 4/2012 | Moriura et al. |
| 8,180,603 B2 | 5/2012 | Blessing et al. |
| 8,187,240 B2 | 5/2012 | Busam et al. |
| 8,211,076 B2 | 7/2012 | Sugiyama et al. |
| 8,268,424 B1 | 9/2012 | Suzuki et al. |
| 8,735,646 B2 | 5/2014 | Beruda et al. |
| 8,802,918 B2 | 8/2014 | Fukudome et al. |
| 8,901,367 B2 | 12/2014 | Sanz et al. |
| 8,979,815 B2 | 3/2015 | Roe et al. |
| 9,072,634 B2 | 7/2015 | Hundorf et al. |
| 9,107,777 B2 | 8/2015 | Kinoshita et al. |
| 9,216,118 B2 | 12/2015 | Roe et al. |
| 9,233,519 B2 | 1/2016 | Yamaguchi et al. |

(56) References Cited

U.S. PATENT DOCUMENTS

| | | | |
|---|---|---|---|
| 9,237,974 | B2 | 1/2016 | Ohashi et al. |
| 9,295,593 | B2 | 3/2016 | Van Malderen |
| 9,468,566 | B2 | 10/2016 | Rosati et al. |
| 9,486,371 | B2 | 11/2016 | Wirtz et al. |
| 9,549,858 | B2 | 1/2017 | Yang |
| 9,707,135 | B2 | 7/2017 | Sheldon et al. |
| 9,713,557 | B2 | 7/2017 | Arizti et al. |
| 9,789,014 | B2 * | 10/2017 | Wright .............. A61F 13/15699 |
| 10,071,002 | B2 | 9/2018 | Bianchi et al. |
| 10,123,916 | B2 | 11/2018 | Weisman et al. |
| 10,307,298 | B2 | 6/2019 | Varona et al. |
| 10,675,195 | B2 | 6/2020 | Greco et al. |
| 10,772,769 | B2 | 9/2020 | Maele |
| 2002/0115969 | A1 | 8/2002 | Maeda et al. |
| 2003/0097105 | A1 | 5/2003 | Chen et al. |
| 2003/0119394 | A1 | 6/2003 | Ranganathan et al. |
| 2003/0119402 | A1 | 6/2003 | Melius et al. |
| 2003/0120231 | A1 | 6/2003 | Wang et al. |
| 2003/0129915 | A1 | 7/2003 | Harriz |
| 2003/0139719 | A1 | 7/2003 | Nanaumi et al. |
| 2003/0143376 | A1 | 7/2003 | Toyoshima et al. |
| 2003/0149414 | A1 | 8/2003 | Mehawej |
| 2003/0167046 | A1 | 9/2003 | Klemp et al. |
| 2003/0175418 | A1 | 9/2003 | Muthiah et al. |
| 2004/0015142 | A1 | 1/2004 | Johnston et al. |
| 2004/0054342 | A1 | 3/2004 | Newbill et al. |
| 2004/0111848 | A1 | 6/2004 | Miyamoto et al. |
| 2004/0116014 | A1 | 6/2004 | Soerens et al. |
| 2004/0167486 | A1 | 8/2004 | Busam et al. |
| 2004/0204697 | A1 | 10/2004 | Litvay |
| 2004/0211361 | A1 | 10/2004 | Suzuki et al. |
| 2005/0165371 | A1 | 7/2005 | Giacometti |
| 2005/0166799 | A1 | 8/2005 | Fuller et al. |
| 2005/0171499 | A1 | 8/2005 | Nigam et al. |
| 2005/0215962 | A1 | 9/2005 | Litvay et al. |
| 2006/0004334 | A1 | 1/2006 | Schlinz et al. |
| 2006/0021695 | A1 | 2/2006 | Blessing et al. |
| 2006/0167424 | A1 | 7/2006 | Chang et al. |
| 2007/0093164 | A1 | 4/2007 | Nakaoka |
| 2007/0197987 | A1 | 8/2007 | Tsang et al. |
| 2008/0103466 | A1 | 5/2008 | Ehmsperger et al. |
| 2008/0215166 | A1 * | 9/2008 | Blessing ........... A61F 13/15658 700/31 |
| 2009/0005752 | A1 | 1/2009 | Suzuki et al. |
| 2009/0076473 | A1 | 3/2009 | Kasai et al. |
| 2009/0087636 | A1 | 4/2009 | Yasuda et al. |
| 2009/0112175 | A1 | 4/2009 | Bissah et al. |
| 2010/0057032 | A1 | 3/2010 | Hardegree |
| 2010/0063470 | A1 | 3/2010 | Suzuki et al. |
| 2010/0100065 | A1 | 4/2010 | Bianco et al. |
| 2011/0046597 | A1 | 2/2011 | Mizutani et al. |
| 2011/0111199 | A1 | 5/2011 | Takatori et al. |
| 2011/0151228 | A1 | 6/2011 | Takatori et al. |
| 2011/0276019 | A1 | 11/2011 | Kakimoto et al. |
| 2012/0029456 | A1 | 2/2012 | Takatori et al. |
| 2012/0071852 | A1 | 3/2012 | Tsang et al. |
| 2012/0089108 | A1 | 4/2012 | Ueda et al. |
| 2012/0175056 | A1 * | 7/2012 | Tsang ................ A61F 13/51405 156/276 |
| 2012/0203191 | A1 | 8/2012 | Maruo et al. |
| 2012/0238977 | A1 | 9/2012 | Oku et al. |
| 2012/0288701 | A1 | 11/2012 | Matsushita et al. |
| 2012/0308799 | A1 | 12/2012 | Yamaguchi et al. |
| 2012/0328861 | A1 | 12/2012 | Hinayama et al. |
| 2012/0328862 | A1 | 12/2012 | Fukudome et al. |
| 2013/0018349 | A1 | 1/2013 | Takatori et al. |
| 2013/0046263 | A1 | 2/2013 | Fukudome et al. |
| 2013/0072890 | A1 | 3/2013 | Yang |
| 2013/0116644 | A1 | 5/2013 | Wei et al. |
| 2013/0178814 | A1 | 7/2013 | Matsushita et al. |
| 2013/0284361 | A1 | 10/2013 | Tsujimoto et al. |
| 2014/0180230 | A1 | 6/2014 | Tsang et al. |
| 2014/0276508 | A1 | 9/2014 | Wright et al. |
| 2014/0276518 | A1 | 9/2014 | Varena et al. |
| 2014/0296817 | A1 | 10/2014 | Malderen |
| 2014/0303582 | A1 | 10/2014 | Wright et al. |
| 2015/0005727 | A1 | 1/2015 | Matsushita et al. |
| 2015/0038929 | A1 | 2/2015 | Malderen |
| 2016/0151213 | A1 | 6/2016 | Bauduin et al. |

FOREIGN PATENT DOCUMENTS

| | | |
|---|---|---|
| EP | 0212618 A1 | 3/1987 |
| EP | 0719531 A1 | 7/1996 |
| EP | 0829245 A2 | 3/1998 |
| EP | 0725616 B1 | 3/1999 |
| EP | 0947549 A1 | 10/1999 |
| EP | 1428581 A1 | 6/2004 |
| EP | 1447066 A1 | 8/2004 |
| EP | 1447067 A1 | 8/2004 |
| EP | 1561442 A1 | 8/2005 |
| EP | 1609448 A1 | 12/2005 |
| EP | 1621166 A1 | 2/2006 |
| EP | 1627618 A1 | 2/2006 |
| EP | 1800638 A1 | 6/2007 |
| EP | 2550946 A1 | 1/2013 |
| EP | 2986263 B1 | 1/2017 |
| EP | 2086487 B1 | 9/2018 |
| GB | 2252047 A | 7/1992 |
| JP | H06190001 A | 7/1994 |
| JP | H10137291 A | 5/1998 |
| JP | 2002159533 A | 6/2002 |
| JP | 2002345883 A | 12/2002 |
| JP | 2003284743 A | 10/2003 |
| JP | 2007236911 A | 9/2007 |
| JP | 2010051697 A | 3/2010 |
| JP | 2010136880 A | 6/2010 |
| JP | 4795612 B2 | 10/2011 |
| JP | 2012075638 A | 4/2012 |
| JP | 2012125597 A | 7/2012 |
| JP | 2012192165 A | 10/2012 |
| JP | 2013010361 A | 1/2013 |
| KR | 100376944 B1 | 6/2003 |
| KR | 100494196 B1 | 9/2005 |
| WO | 9503019 A1 | 2/1995 |
| WO | 9521596 A1 | 8/1995 |
| WO | 0041663 A1 | 7/2000 |
| WO | 2004098473 A1 | 11/2004 |
| WO | 2006007185 A1 | 1/2006 |
| WO | 2007098492 A2 | 8/2007 |
| WO | 2010143635 A1 | 12/2010 |
| WO | 2011128790 A2 | 10/2011 |
| WO | 2012048878 A1 | 4/2012 |
| WO | 2012108331 A1 | 8/2012 |
| WO | 2013099634 A1 | 7/2013 |
| WO | 2015002934 A2 | 1/2015 |

OTHER PUBLICATIONS

3rd Office Action from Chinese Application No. 200780014162.9 filed Feb. 22, 2007, dated Feb. 27, 2013; 8 pages.
First Examination Report issued in corresponding New Zealand Patent Application No. 713158, dated Jul. 19, 2017; [8 pages].
International Preliminary Report on Patentability dated and published Aug. 26, 2008, during the prosecution of International Application No. PCT/US2007/062614.
International Search Report dated Aug. 27, 2014, during the prosecution of International Application No. PCT/US2014/030066.
International Search Report dated Dec. 17, 2007, and published Feb. 21, 2008, during the prosecution of International Application No. PCT/US2007/062614.
International Search Report dated Jan. 12, 2015, during the prosecution of International Application No. PCT/US2014/045027.
International Search Report dated Jul. 30, 2014, during the prosecution of International Application No. PCT/US2014/026148.
International Search Report dated Oct. 28, 2014, during the prosecution of International Application No. PCT/US2014/030051.
Notification of Transmittal of International Preliminary Report on Patentability dated Nov. 24, 2015, during the prosecution of International Application No. PCT/US2014/030051; 48 pages.
Office Action from Chinese Application No. 200780014162.9 filed Feb. 22, 2007, dated Feb. 29, 2012; 9 pages.

(56) References Cited

OTHER PUBLICATIONS

Partial Supplementary EP Search Report, issued in EP Application No. 14763071.9 dated Sep. 23, 2016; 9 pages.
Supplementary EP Search Report issued in EP Application No. 14763071.9 dated Jan. 23, 2017 [18 pages].
Written Opinion dated Aug. 27, 2014, during the prosecution of International Application No. PCT/US2014/030066.
Written Opinion dated Dec. 17, 2007, and published Aug. 22, 2008 during the prosecution of International Application No. PCT/US2007/062614.
Written Opinion dated Jan. 12, 2015, during the prosecution of International Application No. PCT/US2014/045027.
Written Opinion dated Jul. 30, 2014, during the prosecution of International Application No. PCT/US2014/026148.
Written Opinion dated Oct. 28, 2014, during the prosecution of International Application No. PCT/US2014/030051.
Written Opinion of the International Preliminary Examining Authority dated Jun. 5, 2015, during the prosecution of International Application No. PCT/US2014/030051; 32 pages.
Extended EP Search Report, issued in EP Application No. 20156193.3 dated Aug. 21, 2020 [12 pages].

\* cited by examiner

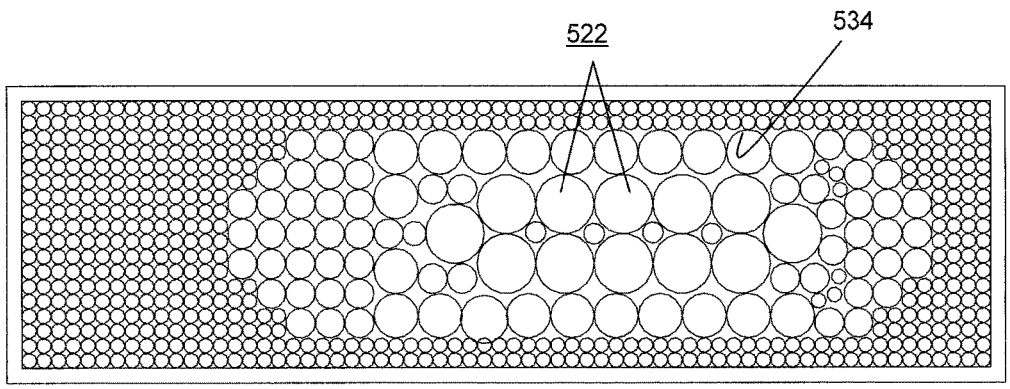
FIG. 15C
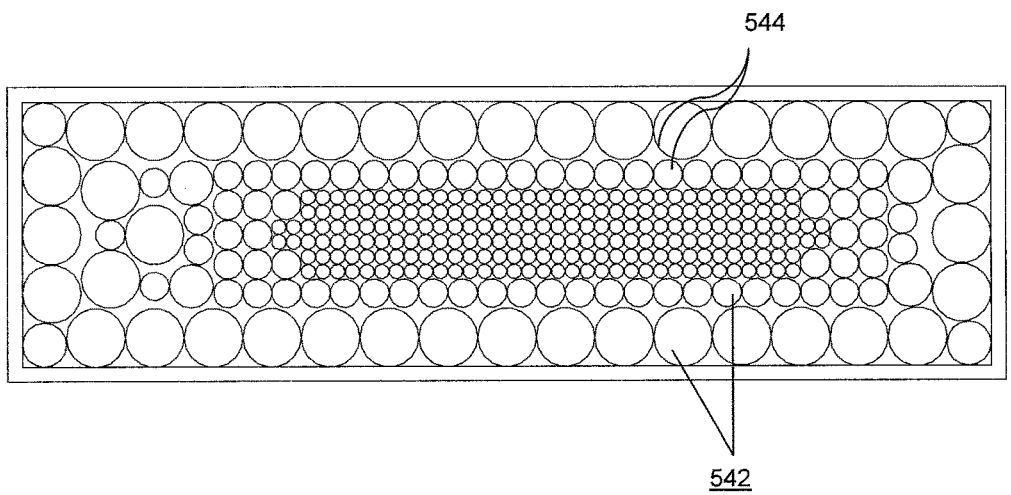
FIG. 15D
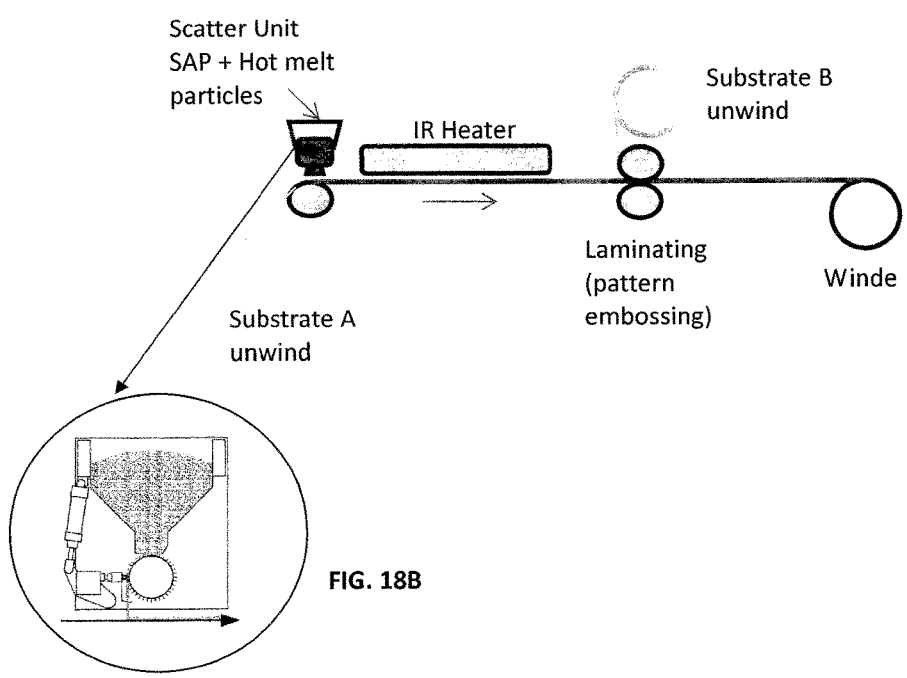
FIG. 18A
FIG. 18B

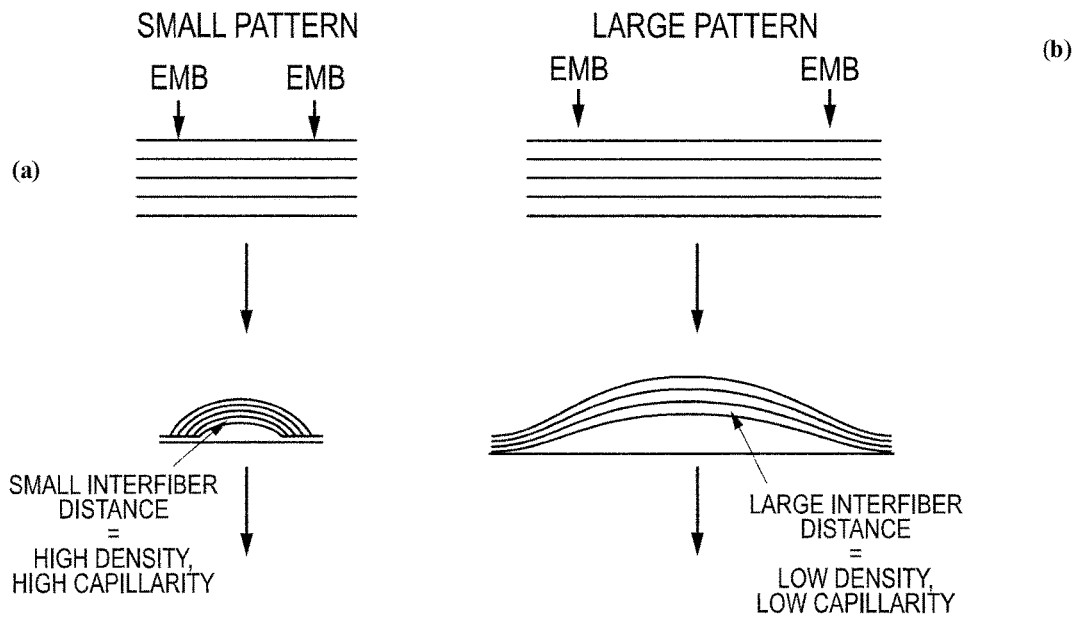
*FIG. 17A*    *FIG. 17B*
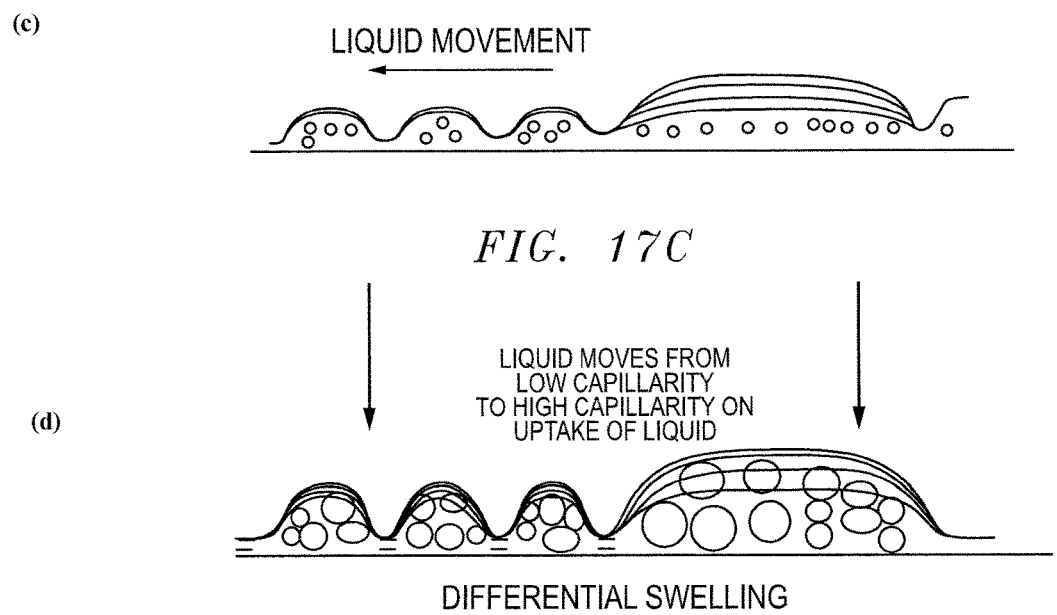
*FIG. 17C*
*FIG. 17D*

METHOD OF MAKING AN ABSORBENT COMPOSITE AND ABSORBENT ARTICLES EMPLOYING THE SAME

The present application is a Continuation application of U.S. application Ser. No. 15/402,003, filed Jan. 9, 2017 (now allowed), which is a Continuation application of U.S. application Ser. No. 14/026,927 filed on Sep. 13, 2013 (now U.S. Pat. No. 9,566,198), which claims the benefit of U.S. Provisional Application Ser. No. 61/801,620, filed on Mar. 15, 2013 (now expired), which disclosure is hereby incorporated by reference for all purposes and made a part of the present disclosure.

BACKGROUND

The present disclosure relates generally to a method of making an absorbent composite. The present invention also relates generally to disposable absorbent articles employing absorbent composites. Such disposable absorbent articles include diapers, training pants, adult incontinence products, bodily exudates absorbing products, feminine hygiene products, and other absorbent products (collectively "disposable absorbent articles").

Prior disposable absorbent articles typically employ three basic structural elements: a topsheet that forms the inner surface, a backsheet that forms the outer surface, and an absorbent core that is interposed between the topsheet and the backsheet. The topsheet is designed to allow liquid to pass from outside the absorbent article through the topsheet and into the absorbent core. The topsheet may be made out of a range of liquid and vapor permeable hydrophilic or hydrophobic materials. The permeability of the topsheet can be increased by using surface activation agents ("surfactants"). Surfactants lower the surface energy or the contact angle of the liquid-solid interface and facilitate the liquid's passage through the topsheet.

The backsheet is designed to prevent fluid from passing from the absorbent core through the backsheet and out of the absorbent article. The backsheet may be made out of an impermeable film that extends the full width of the article or a combination of cloth-like material and impermeable film. The backsheet may also have vapor transmission properties ("breathability") that allow vapor to pass through the backsheet without releasing fluid stored in the absorbent core. The backsheet may also be made from a liquid impermeable but vapor transmittable non-woven material such as spun-bond, melt-blow, spun-bond ("SMS"); spun-bond, melt-blown, melt-blown, spun-bond ("SMMS"); micro, nano, or splitable fibers; spun melt or spun laced; carded; and the like.

The absorbent core is designed to contain and distribute fluid that passes through the topsheet. A typical absorbent core is made out of a high or super absorbent polymer (SAP) stabilized by an absorbent matrix. SAP is commonly made out of materials such as polyvinyl alcohol, polyacrylates, various grafted starches, and cross-linked sodium polyacrylate. SAP can be in the form of particles, fibers, foams, web, spheres, agglomerates of regular or irregular shapes, and film. The absorbent matrix is typically a de-fiberized wood pulp or similar material. The absorbent matrix is very bulky relative to the topsheet, backsheet, and SAP. Most of a diaper's thickness comes from the absorbent core.

Increasingly, consumers of absorbent articles are demanding thinner absorbent articles. To meet these demands, manufactures are decreasing the thickness of absorbent articles by decreasing the amount of absorbent matrix used in absorbent cores. Although the resulting absorbent cores are thinner, they suffer in performance. As the amount of absorbent matrix is reduced, it is less effective in stabilizing the SAP—preventing the SAP from migrating within the absorbent core. As SAP migrates within the core, the absorbent core losses its effectiveness and no longer has uniform absorbency. For example, SAP that is not contained tends to bunch up in wetted areas and is inefficient for handling subsequent discharges.

Manufactures have attempted to solve this problem by creating small, individual SAP pockets or by gluing the SAP. These solutions, however, have been largely unsuccessful. The SAP pockets merely limit the migration to movement within the pockets. However, because there is still a movement of the particles, the absorbent core does not exhibit uniform absorbency. Gluing the SAP stabilizes the SAP, but results in an uncomfortably stiff absorbent core and a loss in the SAP's swelling capacity.

Accordingly, there exists a need for an improved absorbent product that continues the trend of decreasing product thickness, while minimizing product stiffness and otherwise exhibiting excellent absorbency. The specification of U.S. Pat. No. 8,148,598, which is commonly assigned and designates at least one common inventor as the present application, describes a prior improvement to the state of the art and serves as background to the present disclosure. The '598 patent document is hereby incorporated by reference, in its entirety, for all purposes and made a part of the present disclosure. The present disclosure may, in one respect, be regarded as continuing and furthering the effort to provide improved absorbent products and methods of manufacturing.

BRIEF SUMMARY

In one aspect, the disclosure provides improved absorbent composites and methods of making the composite. Various embodiments are disclosed in which aggregates of absorbent particles are strategically located and/or constituted between a top layer and bottom layer, and across the expanse of the composite or core. By varying the position of the aggregates or the restrictions on the aggregates, the performance and capabilities of the absorbent composite may be managed or influenced. In certain embodiments, the aggregates of absorbent particles are situated in containers or pockets. In further embodiments, the size, spacing, arrangement, and\or geometry or shape of the containers or pockets are specifically provided to achieve certain core fluid handling properties.

In one embodiment, a disposable absorbent article includes a chassis body defined by a first end margin and a second end margin longitudinally spaced from the first end margin, the end margins partially defining front and back waist regions that are fastenable about a waist of a user. The article further includes a topsheet, a backsheet, and an absorbent composite disposed between the topsheet and backsheet. The topsheet and backsheet define longitudinal and lateral margins of the chassis body. The absorbent composite includes a first fabric and a second fabric bonded to the first fabric. Furthermore, absorbent particles are adhered between the first and second fabric, wherein the first fabric is intermittently attached to the second fabric to define a plurality of containers situated between the first fabric and the second fabric and containing an aggregate of absorbent particles. The absorbent composite includes regions of containers of absorbent particles aggregates including a primary region having containers of a first size and a secondary region having a plurality of containers of a second size different from the first size.

The present disclosure is of an absorbent composite that, in some embodiments, does not require an absorbent matrix and a novel method of making the absorbent composite. The present document also discloses an absorbent article that incorporates the absorbent composite. The absorbent composite provides for an absorbent article that can be made very thin and pliable, while at the same time retaining enough SAP to provide sufficient absorbency and dry and wet integrity (uniform absorbency). Although using the absorbent composite in a diaper is described, one skilled in the art would readily understand that an absorbent composite made according to the inventive process may be used in a wide variety of absorbent products.

The present disclosure is also directed to an improved absorbent article incorporating the absorbent composite.

In one example, a method is described for manufacturing a composite sheet, comprising the steps of positioning a first fabric to receive particles, depositing particles on the first fabric, applying adhesive to a second fabric, positioning the second fabric relative to the first fabric, and forming bond sites that extend between the first and second fabric. The method may further include an article in which the particles comprise SAP particles, skin care particles, odor absorbing particles, binder particles, ion exchange particles, and combinations thereof. Still further, the method may include the step of coating the particles with a hydrophobic material.

The method may include conforming the first fabric to a surface. The surface may include recesses that form pockets or containers in the first fabric when it is conformed to the surface. The SAP particles may be guided into the pockets formed in the first fabric. Suction may be used to conform the first fabric to the surface. The adhesive applied to the second fabric may be applied in a concentration sufficient to secure an effective amount of dry particles. That concentration is generally between 1 to 100 grams per square meter. More specifically, the adhesive may be applied in a concentration of between 5 and 75 grams per square meter, or even more optimally, between 12 and 50 grams per square meter. The adhesive may be applied in a manner such that the total amount of adhesive engaging particles is between 1 and 100 grams per square meter. The inventive method may further includes a step of applying adhesive to the first fabric before particles are deposited on the first fabric.

The bond sites suitable for the method may be bond lines, which may be continuous or discontinuous and may define pockets or other shapes and designs. Alternatively, the bond sites may be bond points. The bond sites may be positioned relative to particles and/or arranged to prevent straight line particle migration of more than 2 inches.

Alternatively, the method entails positioning a first fabric to receive particles, positioning particles on the first fabric, securing the particles relative to the first fabric, positioning a second fabric over the particles, and forming bond sites that join the first fabric to the second fabric. The bond sites may be discrete points spaced to inhibit the migration of particles. The bond sites may also be bond lines spaced to inhibit the migration of particles, or bond lines that are connected to form a single bond line. The bond lines may be arranged to form pockets within which some particles are positioned. The particles may be SAP particles, skin care particles, odor absorbing particles, binder particles, ion exchange particles, and combinations thereof. The particles may be secured to the first fabric with adhesive, thermal plastic, or combinations thereof. In addition to or in the alternative, the particles may be secured to the second fabric with adhesive, thermal plastic, or combinations thereof. Furthermore, shapes may be formed in the first fabric for receiving particles.

A disposable absorbent article according to the disclosure may comprise a topsheet, a backsheet, and an absorbent core disposed therebetween, wherein at least a portion of one of the backsheet, topsheet, and absorbent core. The absorbent core is an absorbent composite comprising a first fabric, a second fabric bonded to the first fabric, and particles adhered between the first and second fabric. The particles may be SAP particles, skin care particles, odor absorbing particles, binder particles, ion exchange particles, and combinations thereof.

Alternatively, an absorbent layer may be provided that is supported on the backsheet, such that a section of the backsheet provides the second fabric of the absorbent composite. The backsheet may further comprises a first backsheet layer, a second backsheet layer and SAP particles in a concentration of about 20 gsm positioned there between and the second back sheet layer is an SMS having a basis weight in the range of about 10 gsm to 60 gsm. The absorbent layer may be adhered between the first and second fabric with an adhesive concentration of between 1 and 100 grams per square meter. The first fabric may be bonded to the second fabric at discrete points, which discrete points may define pockets. Further, the first fabric may be bonded to the second fabric along a plurality of bond lines, which bond lines may define pockets.

The absorbent core may also comprise a first fabric, a second fabric, bond sites at which the first fabric is connected to the second fabric; and an absorbent layer of particles adhered between the first and second fabric. The particles may be SAP particles and/or other beneficial particles. The absorbent layer may be supported underneath a section of the topsheet, such that the section of topsheet provides the second fabric of the absorbent composite. The absorbent layer may be supported on a section of the backsheet, such that the backsheet section provides the first fabric of the absorbent composite.

In some embodiments, the disposable absorbent article may include a concentration of SAP particles in the absorbent layer of between about 50 and 650 grams per square meter. The SAP particles may also be coated with a hydrophobic material to retard the initial receipt of liquid by the SAP particles in the absorbent layer. The bond sites may define a plurality of continuous lines that inhibit the movement of the SAP particles of the absorbent layer. The continuous lines may be shaped to form pockets between the first and second fabrics. The bond sites may define a plurality of discontinuous lines that inhibit the movement of the SAP particles of the absorbent layer. The discontinuous lines may be shaped to form pockets between the first and second fabric.

In the yet another embodiment, the bonds may be positioned along periphery of pockets of particles. The bonds may form a pattern such as herringbone, bricklayer, circles, triangles, dots, dashes, rectangles, and combinations thereof. The yet another embodiment may also include loose particles positioned between the first and second sheets.

The foregoing has outlined rather broadly the features and technical advantages of the present disclosure in order that the detailed description that follows may be better understood. Additional features and advantages will be described hereinafter. It should be appreciated that the specific embodiments disclosed may be readily utilized as a basis for modifying or designing other structures for carrying out the same purposes. It should also be realized that such equivalent constructions do not depart from the disclosure as set forth in the appended claims. The features which are believed to be characteristic of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding of the present disclosure, reference is now made to the following descriptions taken in conjunction with the accompanying drawing, in which:

FIGS. 15A-15D are simplified illustrations of an absorbent composite according to the present disclosure, with particular attentions to an arrangement of aggregates of absorbent particles across the composite;

FIGS. 17A-17D are simplified illustrations in cross-sectional view of pockets and fluid properties characterizing the arrangement of pockets, in accordance with the disclosure;

FIG. 18A is a simplified schematic of a process of making an absorbent composite according to the disclosure; and FIGS. 18B-18C are illustrations or photographs of exemplary components of the process described in respect to FIG. 18A.

DETAILED DESCRIPTION

Upon review of the detailed description and the accompanying drawings provided herein, it will be apparent to one of ordinary skill in the art that an absorbent composite made according to the present disclosure may be used in disposable absorbent articles, and more particularly, in disposable absorbent articles, such as diapers, training pants or other incontinence products. Accordingly, the present disclosure shall not be limited to the structures and processes specifically described and illustrated herein, although the following description is particularly directed to an absorbent composite that is used in a disposable diaper. The term "absorbent article" or "absorbent garment" with which the present disclosure is associated, includes various types of disposable articles and garments which are placed against or in proximity to the body of the wearer so as to absorb and contain various bodily exudates, bodily fluid, or biofluid.

Perhaps to gain a better understanding and appreciation of the particular contributions and improvements which are introduced in the present disclosure, reference may be first made to the improvements earlier disclosed in U.S. Pat. No. 8,148,598. These earlier improvements are described in respect to FIGS. 1-14. Some of the teachings and suggestions therein may, in addition to serving as background knowledge in the art, translate to certain specific embodiments of the present disclosure (which will become apparent to one skilled in the relevant art given the present disclosure).

Figure 1:
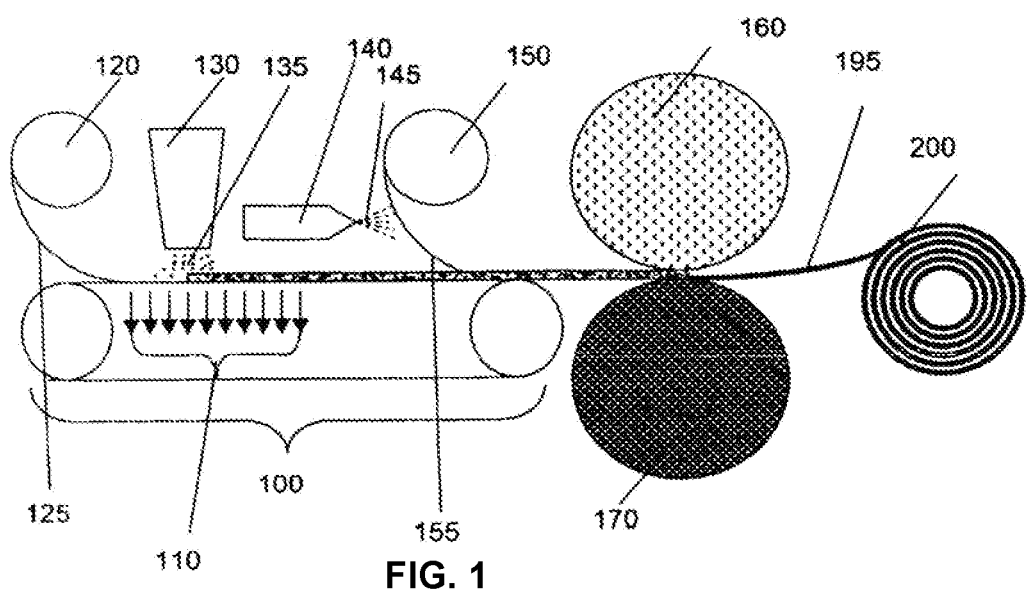
FIG. 1 is a schematic of one embodiment of a method of making an absorbent composite using calendar rolls.

In FIG. 1, a fabric 125 is shown as it is dispensed from roll 120 and carried along a production line on a conveyer belt 100. The fabric 125 may be thermal plastic material that may be a woven, nonwoven, film, or a combination thereof. The fabric 125 is secured to the conveyor belt 100 by a vacuum system 110. The vacuum system 110 serves to confirm the fabric 125 to the convey belt 100.

In one embodiment, the surface of the conveyor belt 100 has recessed portions that form cups in the fabric 125 as the fabric is pulled against the surface of the conveyor belt 100. The surface of the conveyor belt 100 is not limited to constructions that form cups in the fabric but, instead, may be configured with a number of different surface shapes and sizes. Examples include ridges, raised shapes, and holes. In addition, the surface shapes may be distributed uniformly or non-uniformly across the width and length of the conveyor belt. Alternatively, the conveyor belt 100 may be flat. In applications in which the conveyor belt 100 has holes or other similar constructions, the depth of the pockets formed in the fabric 125 may be varied by the force of the vacuum system 110, the elasticity of the fabric 125, or a combination thereof. Additionally, heat may be used to increase the elasticity of the fabric 125 as the fabric is pulled against the surface of the conveyor belt 100. Heat may be applied to the fabric by way of a heated conveyor belt or any other means known in the art. The vacuum 110 may be applied uniformly across the surface of the conveyor belt 100 or at selected locations. For example, in a configuration in which the surface of conveyor belt 100 has depressions, vacuum may be applied only at the depressions.

The SAP particles 135 are then deposited on the fabric 125 by an SAP dispenser 130. The SAP dispenser 130 may be configured to position SAP particles in their desired position on the first fabric or may be configured merely to deposit SAP particles on the first fabric, wherein the SAP particles are position by another means. One skilled the art understands that multiple SAP dispensers 130 may be used. The SAP particles 135 may be deposited, positioned, or both on the fabric 125 by wind or other known methods. Alternatively, the conveyor belt shown in FIG. 1 may be inverted so that the vacuum system 110 applies suction from above. In such a configuration, the fabric 125 is carried over a supply of SAP particles 135 and the SAP particles are held onto the surface of fabric 125 by vacuum system 110. In an alternative embodiments, SAP dispenser 130 may include skin care particles such as ion exchange resins, deodorant, anti-microbial agents, binder particles, or other beneficial particles. Further, although the preferred embodiment is directed to SAP particles, the methods discloses herein can be used with any combination of the above referenced particles, including combinations that do not include SAP. Alternatively, separate dispensers advantageously positioned along the production line (not shown) may be used to deposit different types of particles such as, for example, skin care particles.

The SAP particles 135 are positioned and concentrated on the fabric 125 according to a number of alternative methods. In one embodiment, the vacuum system 110 and fabric 125 may be configured to allow the vacuum system 110 to pull the SAP particles 135 against the surface of the fabric 125 uniformly or in particular areas. In another embodiment, the shape of the fabric 125 guides the SAP particles 135 into position. For example, when the fabric 125 is shaped to form pockets, the SAP particles 135 roll into the pockets as a result of the vacuum system 110, the vibration of the conveyor belt, wind, the angle of the conveyor belt, or combinations thereof. Alternatively, the SAP dispenser(s) 130 may be positioned and controlled to dispense SAP particles 135 strategically across the surface of fabric 125, which strategic positioning includes but is not limited to alignment or nonalignment with the machine direction, offset, or randomly. Further, SAP may be positioned such that there are zones without SAP particles. Still further, SAP particles may be positioned using adhesive such as by applying adhesive to specific locations on a surface, depositing SAP particles on the surface. Still further, SAP particles may be positioned on both fabrics 125 and 155.

Once SAP particles have been deposited and positioned on fabric 125, a second fabric 155 is introduced into the production line from roll 150. The second fabric 155 may be selected from a variety of materials including spun-bonded thermoplastic or similar woven or nonwoven material, film, or combinations thereof.

The adhesive 145 is applied to the SAP particles 135 in a number of ways. FIG. 1 shows the adhesive 145 applied to the fabric 155. Alternatively, the adhesive 145 may be applied to the fabric 125 and SAP particles 135, fabric 125 before the SAP particles 135 are deposited on the fabric 125, or directly to the SAP particles before they are deposited on the fabric 125. In still another embodiment, the adhesive 145 is applied at the point where fabrics 125 and 155 are jointed together. In still another embodiment, multiple coats of adhesive are applied. For example, adhesive 145 may be applied to the fabric 125 before the SAP particles 135 are deposited, to the SAP particles 135 after they have been positioned, to the fabric 155, or a combination thereof. Alternatively or in addition to the above embodiments, binder particles may be mixed with the SAP particles 135. Additionally, the adhesive may be applied uniformly, randomly, or in a specific pattern, depending the desired absorbent properties of the finished composite.

The adhesive is applied according to a number of methods know to those skilled in the art. For example, the adhesive may be sprayed, rolled, or spun onto the surface of fabric 155. The adhesive may be hydrophobic, hydrophilic, biodegradable, bioderived, or combinations thereof. The preferred adhesive is hydrophobic. The concentration of adhesive in a coat varies between 1 and 100 grams per square meter ("GSM"). Optimally, the concentration is between 5 and 75 GSM. In a preferred embodiment, the concentration is between 12 and 50 GSM. Additionally, enough adhesive should be applied to cover at least 25% of the targeted area.

Fabrics 125 and 155 are then bonded together. FIG. 1 shows a thermal bonding system in which calendar rolls 160 and 170 are used. However, other bonding systems/methods may be used. For example, the ultrasonic bonding system of FIGS. 4 and 5 may be used. Adhesive 145 retains the SAP particles 135 in a relatively fixed position with respect to the fabrics during the bonding process and subsequent to the bonding process. The bond pattern may be aligned with the distribution of the SAP particles 135. Alternatively, the bond pattern may not be aligned with the distribution of the SAP particles 135. In such embodiments, the bonding equipment may be adapted to nudge the SAP particles 135 aside prior to bonding or to bond through the SAP particles 135. These embodiments eliminate the need to synchronize the pond points with the distribution of SAP particles.

Fabrics 155 and 125 are shown as two materials. However, one skilled in the art understands that the fabrics may actually be part of the same material. In such a configuration, the unitary fabric is folded to cover the SAP particles. Alternatively, the edges of fabric 125 may be folded prior to applying the second fabric 155. In embodiments in which fabrics 125 and 155 are separate, fabrics 125 and 155 may be the same or a different material. Additionally, fabric 155 may be sized to cover specific areas, such as the center section, of fabric 125.

Once the fabrics have been bonded together, the absorbent composite 195 is collected on rewinder 200.

Figure 2:
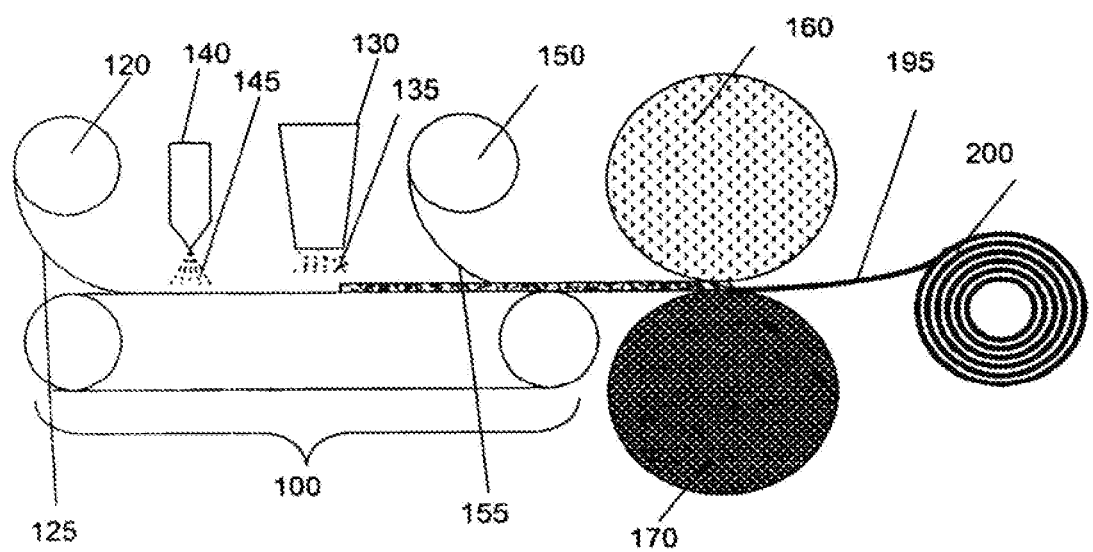
FIG. 2 is a schematic of another embodiment of a method of making the inventive absorbent composite using calendar rolls.

In a method illustrated in FIG. 2, the fabric 125 is transported along the conveyer belt 100. As fabric 125 is transported along the conveyer belt 100, a thin coat of adhesive 145 is applied to fabric 125. As with the method of FIG. 1, the adhesive may be applied uniformly, randomly, or in a specific pattern, depending the desired absorbent properties of the finished composite. Although the adhesive 145 is shown being applied before the SAP Particles 135 are deposited, alternate embodiments are envisioned. For example, the adhesive may be applied according to the embodiments described with respect to FIG. 1.

Following the application of the adhesive, SAP particles 135 are deposited and positioned on the fabric 125. The SAP particles 135 may be deposited directly on fabric 125, as shown in FIG. 2, or indirectly, such as by wind blowing SAP particles across fabric 125. The weight of the SAP particles aids in securing the fabric 125 to the conveyor belt 100. Additionally, the SAP particles may be positioned in a manner similar to that disclosed for FIG. 1.

A second fabric 155 is then fed into the production line from roll 150. The second fabric is positioned to cover the SAP particles 135. The adhesive 145 prevents the SAP particles from moving freely between the two fabrics. The resulting sandwiched construction is then transported to the calendar rolls for thermal bonding. As described with respect to FIG. 1, the bond pattern may be aligned or not aligned with the SAP particles 135. The absorbent composite 195 is then collected by rewinder 200. As described with respect to FIG. 1, fabrics 125 and 155 may be part of a single sheet. Additionally, the fabrics may be folded in the manner described for FIG. 1. In another embodiment, the fabric 125 may be coated with adhesive and pressed on a supply of SAP particles.

Figure 3:
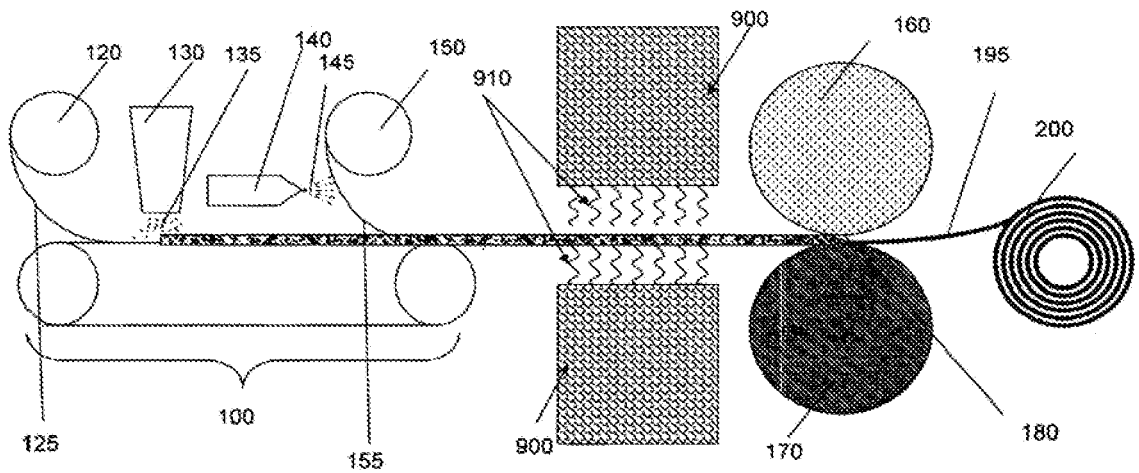
FIG. 3 is a schematic of the method shown in FIG. 1 with an additional energy source.

FIG. 3 is similar to FIGS. 1 and 2, except that an energy source 900 such as an oven or microwave generator is positioned along the assembly line. The energy source applies heat and or radiation 910 that can be used to melt thermal plastic binder. The amount of heat may also be regulated to melt specific types of particles or fibers, specific sections of the fabrics, or only the outer layers of particles/binder.

Figure 4:
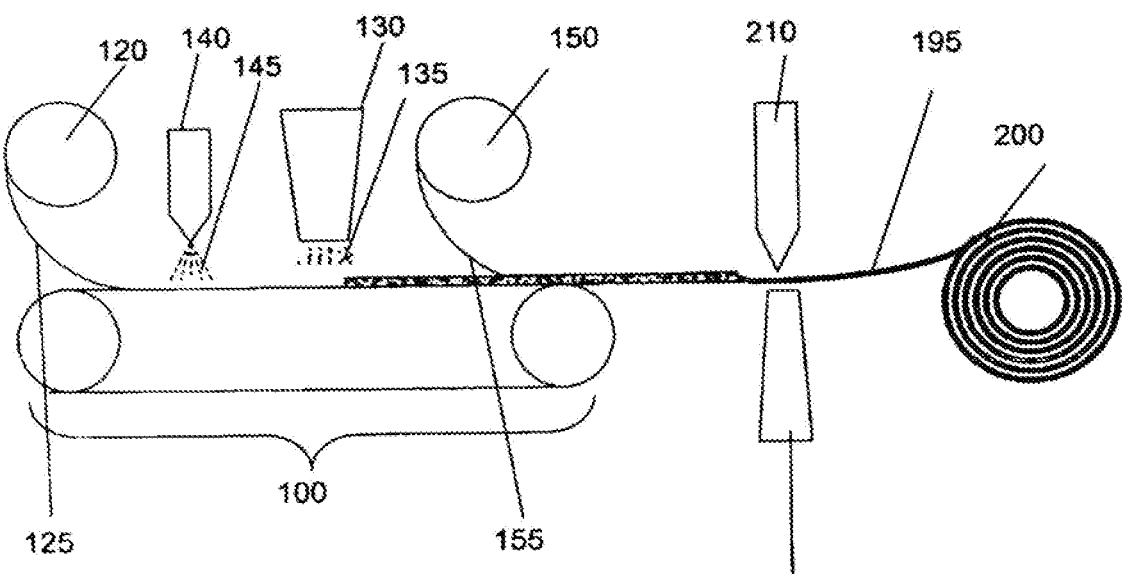
FIG. 4 is a variation of the method shown in FIG. 1 that uses ultrasonic bonding techniques instead of calendar rolls.
Figure 5:
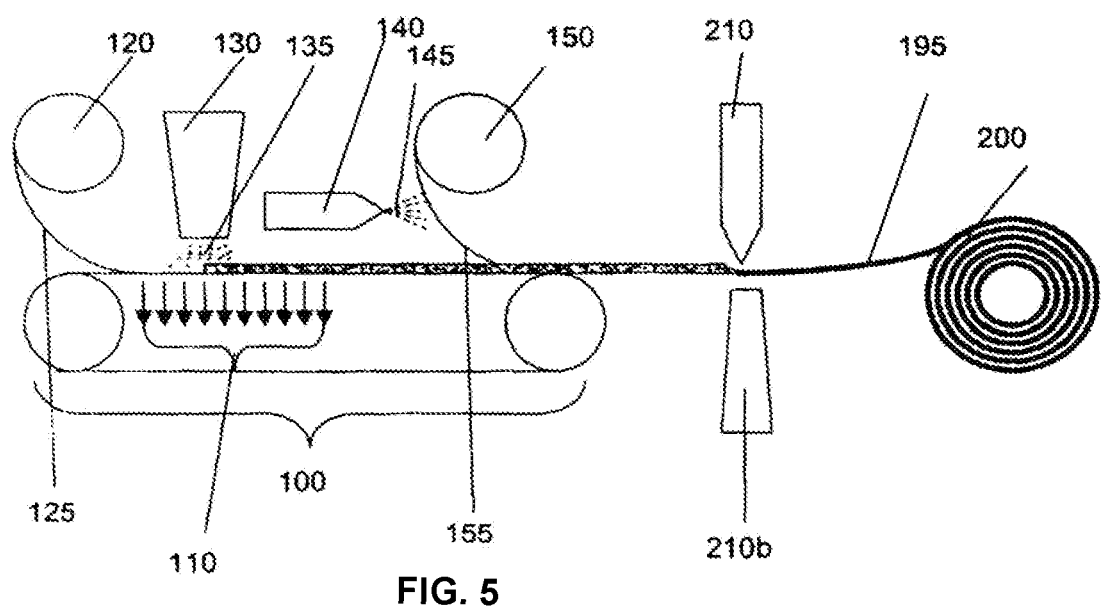
FIG. 5 is a variation of the method shown in FIG. 2 that uses ultrasonic bonding techniques instead of calendar rolls.

FIGS. 4 and 5 are similar to FIGS. 1 and 2, except that the fabrics are bonded together using ultrasonic bonds. FIGS. 4 and 5 show an ultrasonic bonding system (210a and 210b). It is readily understood that FIGS. 1-5 show different embodiments of the novel method and that aspects of the various methods may be advantageously combined depending on the need.

Important to all combinations, however, is the amount of adhesive 145, binder particles, or combinations thereof applied to the SAP particles 135 and the strength of the bonds. As noted with respect to FIG. 1, the optimal concentration of adhesive is between 12 and 50 GSM, though other concentrations are acceptable. In all embodiments, it is important that the concentration of adhesive 145 be high enough to inhibit the migration of SAP particles 135. The concentration should not be so high, however, that it coats the SAP particles 135 and reduces SAP swelling. The adhesive should only inhibits the migration of enough SAP particles 135 to assure uniform absorbency. Although not shown, one skilled in the art understands that the energy source 900 shown in FIG. 3 can also be applied in the configurations shown in FIGS. 2, 4 and 5.

Figure 6:
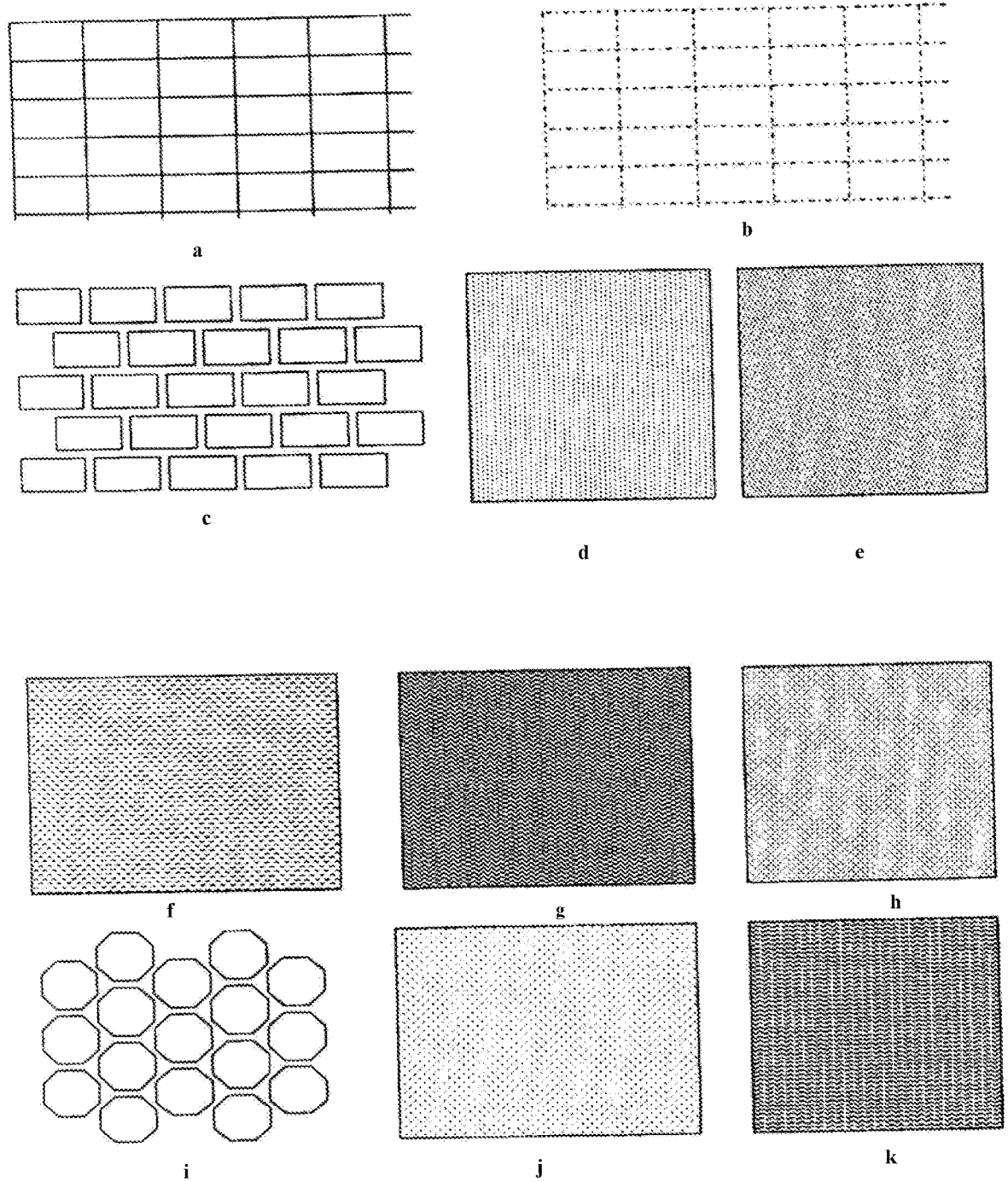
FIG. 6 is an illustration of various potential bonding patterns that may be used in the method and absorbent article.
Figure 6:
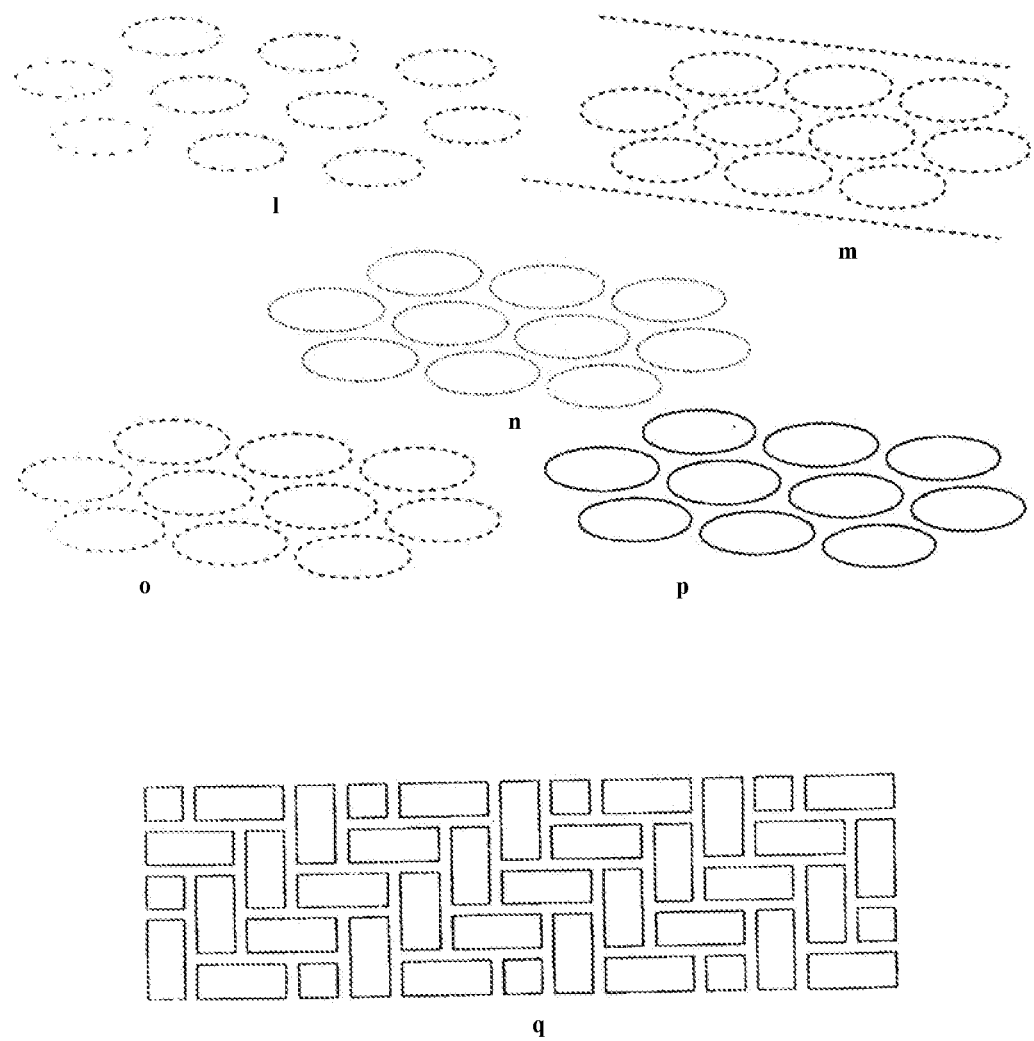

FIG. 6 (a) through (q) show various bonding patterns contemplated by the method. The bonding patterns may completely enclose an area, partially enclose an area, or provide local bonding zones. The lines and points indicate the bond sites. The solid lines depict bond lines. The bond lines may form open shapes or enclosed shapes, such as can be found in examples (a) and (c), which depict continuous bond lines that completely enclose pockets of SAP particles 135 or, as in example (g), separate distinct regions of the absorbent composite. The dashed lines, such as can be found in examples (b) and (m), are discontinuous bond patters that do not completely enclose pockets of SAP particles 135. In these configurations, the migration of dry SAP particles is inhibited by the adhesive and continuous or discontinuous bond patters. Discontinuous pond patters may be substituted for continuous bond patterns and visa versa. Further, though the FIG. 6 shows either continuous or discontinuous bond patters, combinations of discontinuous and continuous bond patters may be used.

Figure 7:
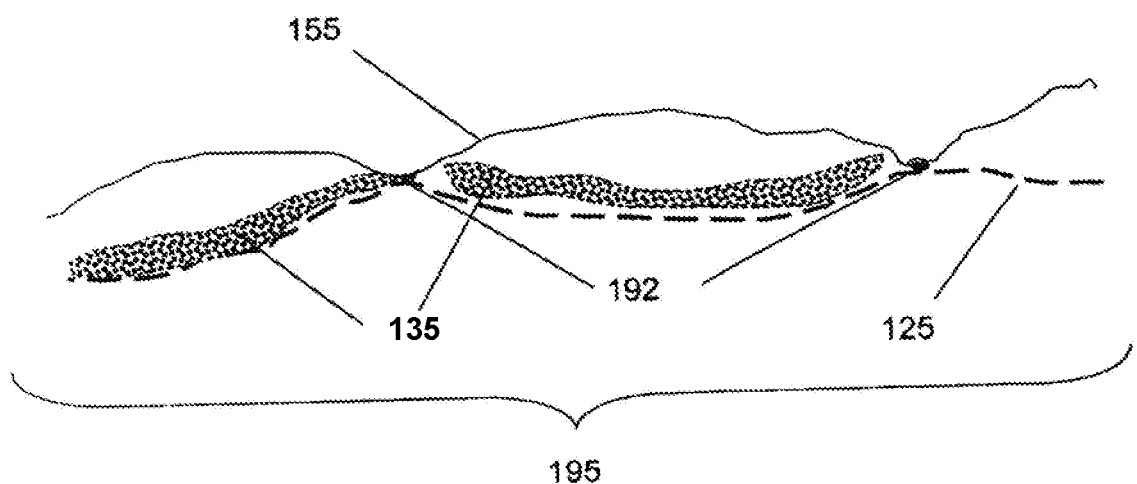
FIG. 7 is a cross sectional illustration of a pockets formed by the method and utilized in the absorbent article.

FIG. 7 shows a partial cross-section of an absorbent composite 195. FIG. 7 shows how bonds 192 may act to separate pockets of SAP particles 135. As noted with respect to the bonding pattern, SAP particles 135 may be entirely enclosed in pockets defined by the bonding pattern, partially enclosed in pockets defined by the bonding pattern or merely inhibited by the bonding pattern. Inhibited in this context means the SAP particles 135 cannot move directly from one area of the core to another area, but instead, must move around bond sites.

Notably, multiple functions or advantageous properties are obtained in the absorbent composite by varying the amount of SAP particles, the type and number of fabrics used, and construction variables such as, the ratio of SAP to adhesive, and applying the absorbent composite at various locations in the article. Such manufacturing and design techniques may be incorporated into structural designs and methods of the present disclosure.

Additionally, one skilled in the art understands that the process for constructing a single absorbent composite described above may be modified to produce a multiple, laminated absorbent composite. In structures comprising multiple layers, the layers may be sheets of absorbent composite 195 that are laminated together to form a single structure or alternating layers of fabric and SAP particles 135 that form a single structure. One skilled in the art understands that alternating layers may be achieved by applying adhesive to the top of fabric 155 (FIG. 1), applying a second layer of SAP particles 135, and a third fabric (not shown). Similarly, additionally layers may be added, limited only by the maximum thickness suitable for the bonding process.

The SAP particles 135 may be coated with a miscible, hydrophobic material. The coating acts as a barrier or membrane that initially slows the liquid uptake, thereby saving SAP capacity for additional or secondary discharges. In this regard, the coating evens out the absorbency rates between discharges. In the processes shown in FIGS. 1 to 5, the coating may be applied prior to the adhesive 145 being applied, after the adhesive 145 is applied, or at the same time. Alternatively, the adhesive may be mixed with the coating material.

In one example, a light coating of mineral oil is applied over the SAP particles 135. The coating retards the initial uptake by the SAP particles and allows more time for the liquid to spread out in the article. Preferably, the mineral oil is applied at a concentration of about 0.00001 grams per gram of SAP to about 0.1 grams per gram of SAP (depending on the particular product design). Alternatively, the mineral oil may be applied in specific target zones. In this way, the received liquid is encouraged to initially spread to uncoated areas before the coated areas are activated and begin to swell.

An absorbent composite manufactured by the above-described process may be used for a disposable absorbent article or as one or more of the components of a disposable absorbent article. The components of an absorbent article include the backsheet, topsheet, absorbent core, containment walls or cuffs (including leg gathers), backsheet/absorbent core composite, topsheet/absorbent composite, and combinations thereof. Such constructions are described below in more detail.

Figure 8:
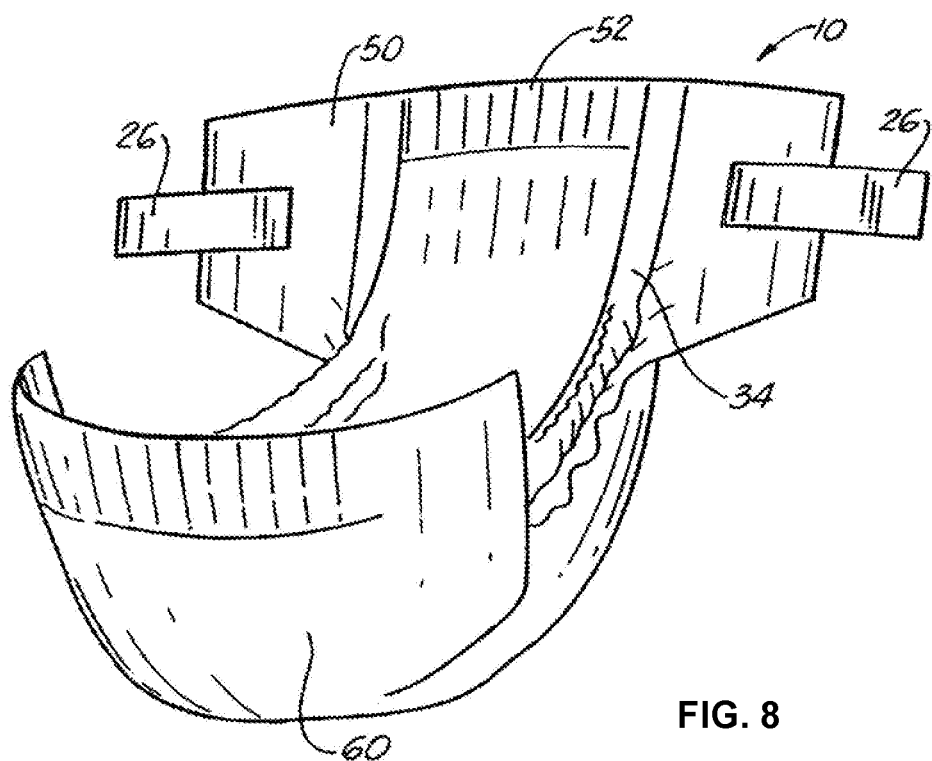
FIG. 8 is a perspective view of a disposable absorbent article embodying the absorbent composite.

FIG. 8 is a perspective view of a disposable absorbent article in the form of a diaper 10. Diaper 10 comprises a topsheet 50, a backsheet 60, and an absorbent core (not shown). The diaper further comprises upstanding barrier cuffs 34 which extend longitudinally along the diaper and are elasticized to conform to the buttocks of the wearer. Additionally, the diaper includes an elastic band 52 and fastening elements 26. Element 26, in use, extends to and engages the corresponding opposing end of the diaper to secure the diaper about the wearer.

Figure 9:
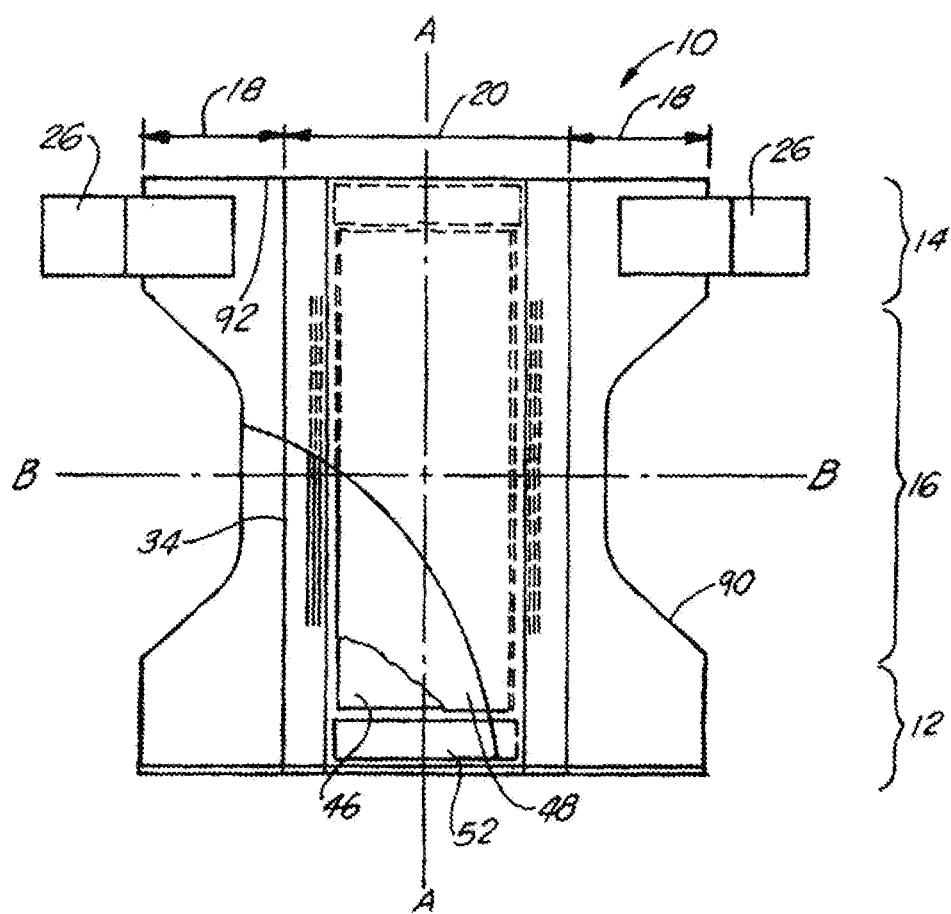
FIG. 9 is a top plan view of the disposable absorbent article of FIG. 8 in a flat and extended condition.

FIG. 9 illustrates a composite web structure of the diaper 10 of FIG. 8 in a generally flat and unfolded configuration. As will be explained further below, the web structure may be subsequently trimmed, folded, sealed, welded and/or otherwise manipulated to form a disposable diaper 10 in a finished or final form. To facilitate description of the diaper 10, the description refers to a longitudinally extending axis AA, a laterally extending central axis BB, a pair of longitudinally extending side edges 90, and a pair of end edges 92 which extend between side edges 90. Along the longitudinal axis AA, the diaper 10 includes a first end region or front waist region 12, a second end region or back waist region 14, and a crotch region 16 disposed therebetween. Each of the front and back waist regions 12, 14 is characterized by a pair of ear regions or ears 18, which are located on either side of a central body portion 20 and extend laterally from the side edges 90. A fastening structure 26 (e.g., a conventional tape fastener) is affixed to each of the ears 18 along the back waist region 14 of diaper 10.

When the diaper 10 is worn about the waist, the front waist region 12 is fitted adjacent the front waist area of the wearer, the back waist region 14 is fitted adjacent the back waist area, and the crotch region 16 fits about and underneath the crotch area. To properly secure the diaper 10 to the wearer, the ears 18 of the back waist region 14 are brought around the waist of the wearer and toward the front and into alignment with the ears 18 of the front waist region 12. The securing surface may be located on or provided by the interior or exterior surface of the front waist region 12. Alternatively, the fasteners 26 may be located on the ears 18 of the front waist region 12 and made securable to the ears 18 of the back waist region 14.

Figure 10:
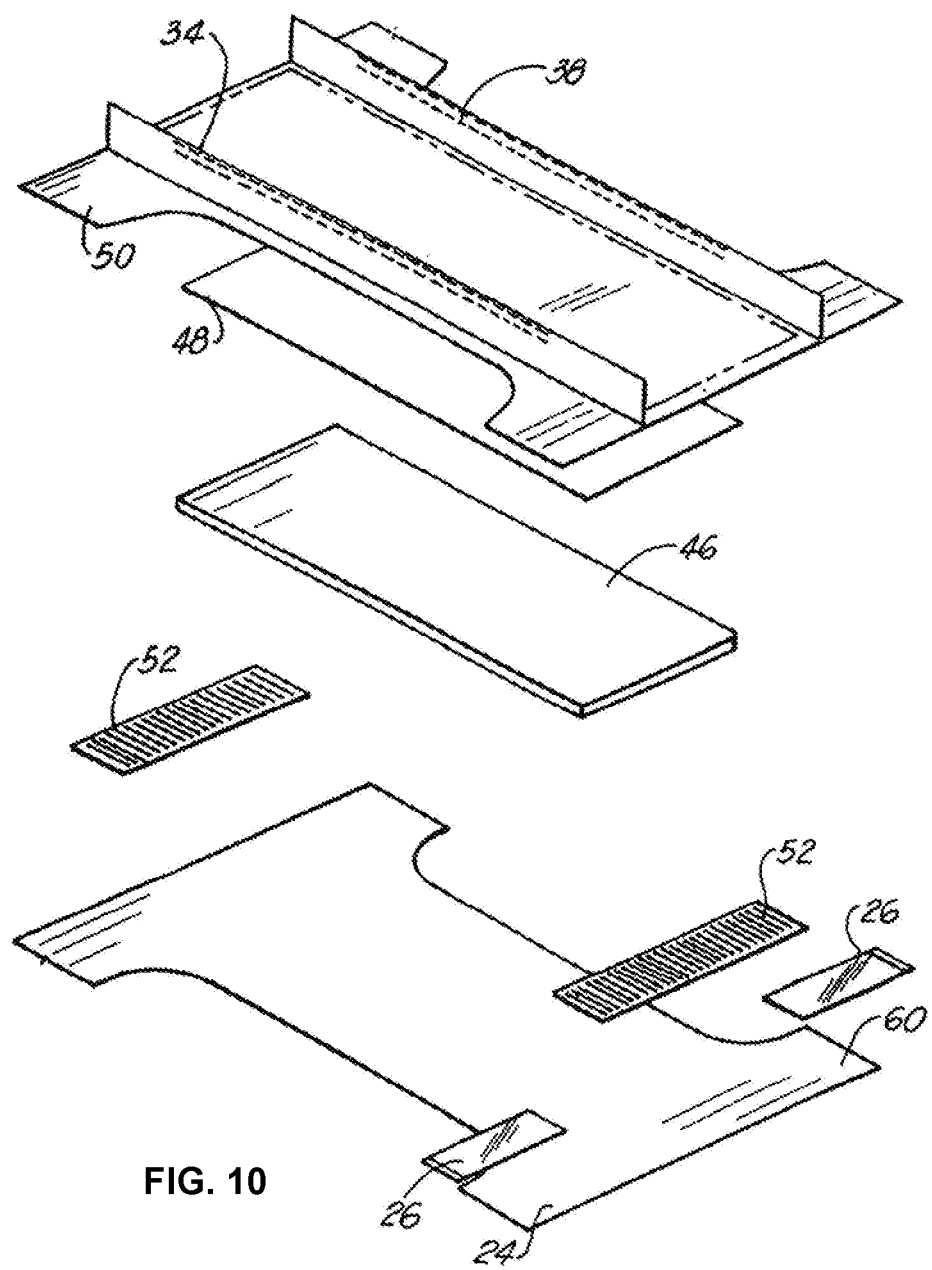
FIG. 10 is an exploded view of the disposable article of FIG. 8.

FIG. 10 is an exploded view of the diaper of FIGS. 8 and 9. A suitable diaper structure typically employs at least three layers. These three layers include a backsheet 60, an absorbent core 46, and a topsheet 50. The diaper structure mayor may not contain a pair of containment walls or leg cuffs 34 disposed upwardly from the topsheet 50 and preferably equipped at least with one or more spaced apart, longitudinally elastic members 38. It will be shown below that any of these diaper elements or a combination of these elements may be constructed with or using the absorbent composite 195. Additionally, an acquisition layer 48 could be added to improve performance.

Backsheet

As mentioned above, the diaper 10 employs a backsheet 60 that covers the core 46 and preferably extends beyond the core 46 toward the side edges 90 and end edges 92 of the diaper 10. In one aspect of the invention, the backsheet 60 is constructed from a single-layered material sheet of absorbent composite 195. In such a configuration, fabric 125 is positioned as an outer surface of the backsheet 60.

Additionally, an alternative structure could be used for gel blocking. For an application using gel blocking, a backsheet of the inventive disposable absorbent article is relatively thin and provides improved flexibility. When dry, the backsheet is soft and breathable, but upon wetting, a thin, gel blocked layer is formed (i.e., on the inner surface of the backsheet) which renders the backsheet substantially liquid impervious. The gel blocked layer is formed by the swelling of the SAP particles 135.

Topsheet

Similarly, the absorbent composite 195 may be utilized with or as the topsheet of an absorbent garment. The topsheet 50 is preferably soft, compliant, exhibits good strikethrough and a reduced tendency to rewet from a liquid pervious material. The topsheet 50 is placed in close proximity to the skin of the wearer when the diaper 10 is worn. In this way, such a topsheet 50 permits bodily discharges to rapidly penetrate it so as to flow toward the core 46 more quickly, but not allowing such discharges to flow back through the topsheet 50. The topsheet 50 may be constructed from anyone of a wide range of liquid and vapor permeable hydrophilic materials. The surface(s) of the topsheet may be treated with a surfactant so as to facilitate liquid transfer therethrough, especially at a central zone or area of the topsheet located over the core and an inner surface of the core. The topsheet may also be coated with a substance having rash preventing or rash reducing properties (e.g., aloe vera).

In one example, the topsheet 50 is formed from an absorbent composite 195 that covers substantially the entire area of the disposal absorbent article 10, including substantially all of the front waist region 12, back waist region 14, and crotch region 16. Further, the ear layer of the inner region 18 is formed from the same single topsheet material and, thus, may be referred to as being unitary with the topsheet 50 in forming lateral extensions of the topsheet material. Alternatively, the topsheet 50 may be formed from multiple different materials which vary across the width of the topsheet 50. Such a multiple piece design allows for creation of preferred properties and different zones of the topsheet.

Absorbent Core

Figure 11:
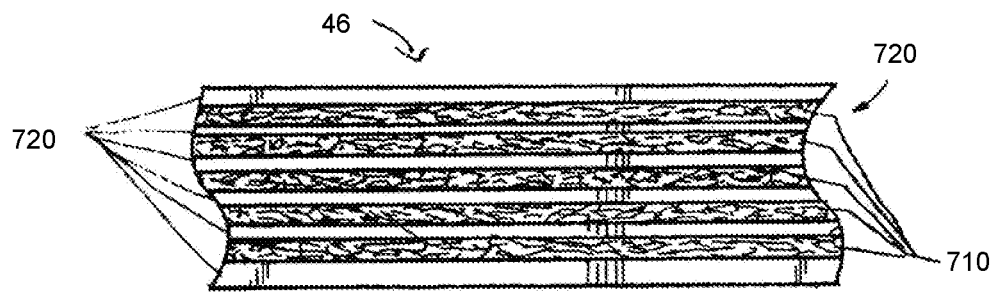
FIG. 11 is a partial cross-sectional view of an absorbent core utilizing the absorbent composite and employed by an absorbent article.
Figure 12:
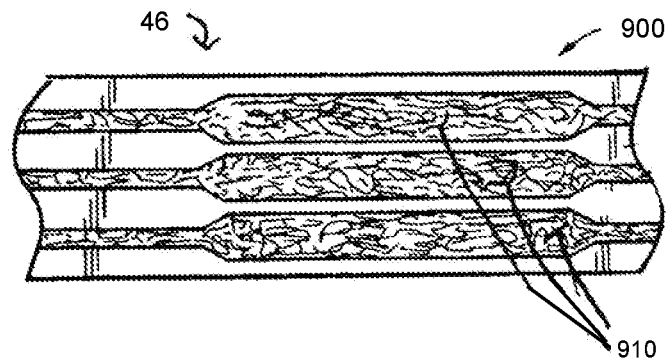
FIG. 12 is partial cross-sectional view of an absorbent core utilizing an alternative embodiment of the inventive absorbent composite and employed by an alternative absorbent article.

In addition to or as an alternative to the above examples, the absorbent core of the disposable absorbent article may be constructed from the absorbent composite 195, laminated layers of absorbent composite 195 (not shown) or multiple layers of SAP particles 135 and fabric. FIGS. 11 and 12 depict cross sectional views of alternating layers of SAP particles 135 and fabric that form a multi layered absorbent composite 700 and 900, respectively. As shown in these drawings, the core 46 may be comprised of distinct layers of SAP particles 135 (710 and 910). The layers may be uniform or non-uniform, depending on the intended application. In the non-uniform multi layered absorbent composite 900, the concentration of SAP particles 135 may vary within a given layer, between layers, or combinations thereof.

FIG. 11 depicts a composite structure 700 in which SAP particle layers 710 and fabric layers 720 are alternated to form the completed composite structure 700. The layered design can also be constructed by bonding together sheets of absorbent composite, folding a unitary sheet of absorbent composite, or constructing absorbent composites with multiple layers during the manufacturing process. In folded applications, the composite fold may be a C-fold, Z-fold, V-fold, W-fold or combinations thereof. Further, the folds may be open, closed, or overlapping.

FIG. 12 depicts multi layers absorbent composite 900. As shown in FIG. 12, high concentrations areas of SAP particles 910 may be strategically positioned to provide additional absorbency in specific regions such as the crotch of an absorbent article. One skilled in the art understands that the high concentration areas may be offset to control the amount and direction of liquid penetration. Additionally, the layer with zones of high concentrations may be combined with layers of substantially uniform layers. Alternatively, the high SAP concentration areas can be formed by positioning multiple layers of absorbent core.

The core may be configured to extend substantially the full length and/or width of the disposable absorbent article. Preferably, however, the core is disposed or is otherwise concentrated at the crotch region of the article. In various embodiments, the core extends to the edges of the article and the SAP particles 135 are concentrated in the crotch region or another target zone of the article. In still another embodiment, the particles can be a combination of SAP particles, skin care particles such as ion exchange resins, deodorant, anti-microbial agents, binder particles, or other beneficial particles.

Containment Walls

Figure 13:
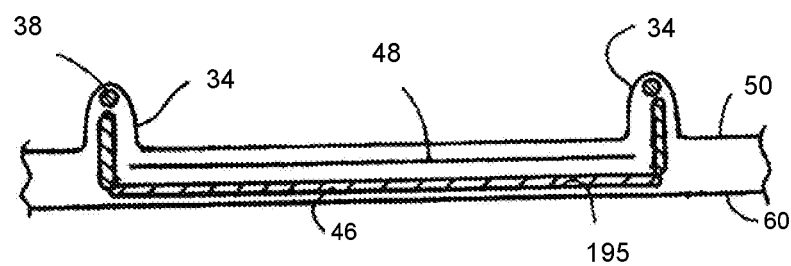
FIG. 13 is a cross-sectional view of an absorbent article employing in the leg cuffs an absorbent composite.
Figure 14:
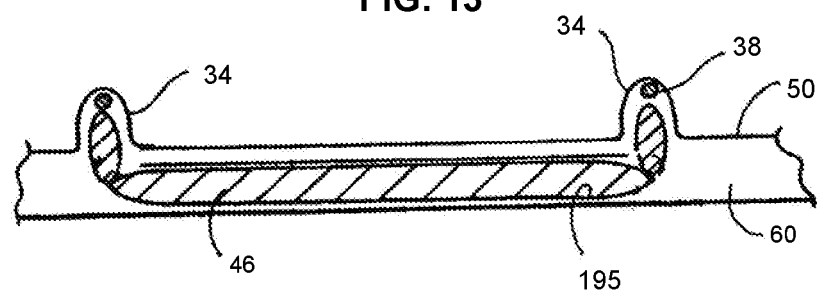
FIG. 14 is a cross-sectional view of an absorbent article employing in the leg cuffs a saturated absorbent composite.

Now turning to FIGS. 13 and 14, the disposable absorbent article 10 utilizes a pair of containment walls or cuffs 34 which employ the absorbent composite 195. Each containment wall 34 is a longitudinally extending wall structure preferably positioned on each side of the core 46 and spaced laterally from the longitudinal center. The longitudinal ends of the walls 34 may be attached, for example, to the topsheet 50 in the front and rear waist regions 12 and 14. Preferably, the ends of the containment wall 34 are tacked down inwardly and attached, for example, by adhesive to the web structure. Such a construction effectively biases the containment wall 34 inwardly and is generally considered to cause containment wall 34 to exhibit improved leakage prevention properties.

FIG. 13 provides a cross-sectional view of a diaper 10. The diaper 10 includes backsheet 60, absorbent core 46, acquisition layer 48, and topsheet 50. As shown in FIG. 13, the core is an absorbent composite 195. The diaper 10 also includes a pair of containment walls or cuffs 34 which are formed by folding the topsheet 50 and wrapping it about the ends of the absorbent composite 195. Alternatively, the absorbent composite 195 in the cuffs 34 may be distinct from the absorbent core 46.

Preferably, the containment walls 34 are equipped with elastic members 38, which extend along a substantial length of the containment walls 34. In a common application, the elastic members 38 are placed within the containment walls 34, preferably at the top of the containment walls 34 while in a stretched condition and the glued to the containment walls at least at their ends. When released or otherwise allowed relaxing, the elastic members 38 retract inwardly. When the article 10 is worn, the elastic members 38 function to contract the containment walls 34 about the buttocks and the thighs of the user in a manner, which effects a seal between the article 10, the buttocks and the thighs. The core 46 may be a single sheet of absorbent composite 195 or multilayered, as described above.

FIG. 13 depicts the configuration of the containment walls 34 when it is soft and dry. FIG. 14, on the other hand, depicts the containment walls after wetting, in which the absorbent composite 195 has swollen to dispose the containment walls 34 in a resiliently, erect position. Unlike traditional leg cuffs in the prior art, the resiliently erect containment walls 34 resists flattening (e.g., when the wearer sits down) and, thereby, ensures leakage prevention, especially of explosive, liquefied bowel movements and rapid discharges of urine.

Optional Layers

The disposable absorbent article may employ additional layers including an acquisition layer or surge layer 48, preferably situated between the topsheet and the core (e.g., FIG. 10). One function of such an acquisition layer is to spread out or disperse liquid flow so that liquid is distributed more evenly over the core surface. This serves to slow down the flow so that the liquid has adequate time to be absorbed by the core. The acquisition layer also serves to prevent the core from being saturated locally, while a substantial remainder of the core is not absorbing any liquid.

Tape Tabs

The disposable absorbent article must be secured to the wearer. This is most important with respect to diapers since diapers are not pulled up by the wearer, like training pants or incontinent briefs, but are fastened around the wearer. Securing elements compliment the elastic members by effecting a quasi-seal between the wearer and the waistband and leg cuffs, so that liquid is contained within the article which is then absorbed; in other words, so that it does not leak through gaps between the wearer and the edge of the article. The securing elements may be adhesive, mechanical fasteners hook and loop features, or conceivably strings, i.e., anything that will secure one end of the article to the longitudinally opposite end. The securing elements may also be co-adhesive such that they adhere to each other but not other materials.

In the examples shown in the Figures (see, e.g., FIG. 10), the article 10 is affixed to the wearer by tape fasteners 26 which are permanently affixed to (e.g., sewn directly into) the backsheet 60. Tape fasteners 26 are contacted with the transversely opposite ear 22 extending from the backsheet, where they remain affixed due to adhesive compound applied to the fasteners 26. Alternatively, the article 10 may be training pants, pull-on diapers, and the like. In this configuration, the article 10 mayor may not have tape fasteners 26.

Waistband

Waistbands employing elastic members 52 are positioned along the transverse portion of the article 10 so that when worn, the waistbands are positioned along the waist of the wearer. Generally, the waistband preferably creates a quasi-seal against the waist (transverse elastic members 52) so that liquid waste does not leak from the regions between the waist elastic and the waist of the wearer. The quasi-seal is significant because, although the liquid may be eventually absorbed by filler material, the assault of liquid by the wearer may overwhelm the absorption rate capacity of the filler material. Hence, the waistbands contain the liquid while it is being absorbed. Secondly, the waistbands may have a capacity to absorb liquid (see, e.g., U.S. Pat. No. 5,601,544, which is hereby incorporated by reference).

Figures 15A, 15B:
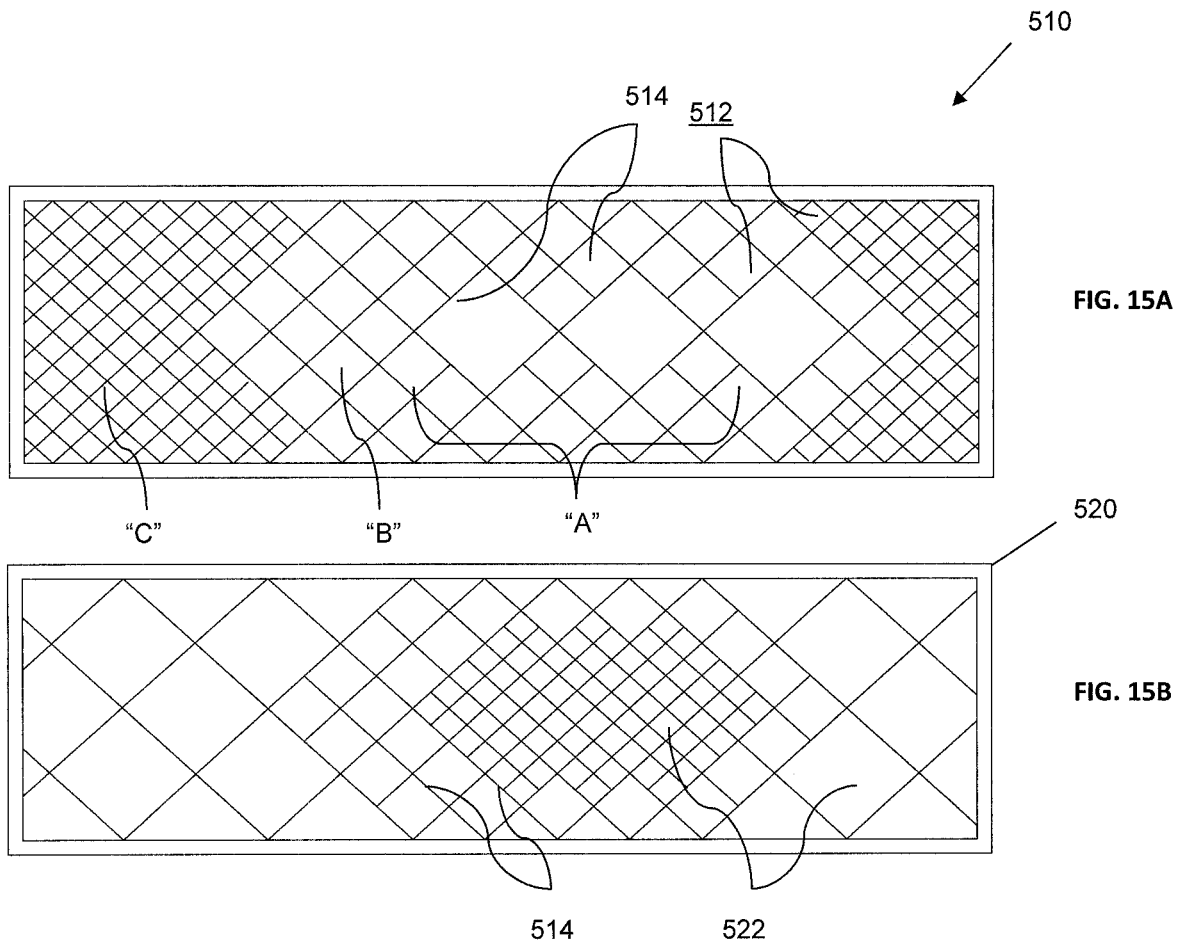

Aggregate (and Embossing) Patterns and Material Selection for Fluffless Absorbent Composites The simplified illustrations of FIGS. 15A-15D present absorbent composites 510 with particularly advantageous arrangements of aggregates 512 of absorbent particles, according to the present disclosure (with like reference numerals used to indicate like elements). Referring first to FIG. 15A, each of the aggregates on the absorbent composite 510 are represented by the diamond-shaped enclosure 514 in the pattern. In preferred embodiments, SAP is employed as the absorbent particles in the aggregates. Furthermore, SAP aggregates in each of FIGS. 15A-15D are preferably maintained in place and stabilized by physical entrapments or containers provided by the engagement of a first fabric disposed generally above the SAP aggregate with a second fabric disposed generally beneath the SAP aggregate. Thus, in an alternative view of FIG. 15A, the diamond units represent the outline of the containers or pockets, reflecting in particular embodiments, the engagement of the top fabric with the bottom fabric, as previously described herein.

As described previously, the absorbent performance of the SAP can be affected by the size and structure of the container. As SAP becomes more saturated, its permeability is reduced. Water cannot pass through the SAP particle due to the high level of water already contained within the SAP particle and eventually the SAP can completely halt the passage of further fluid through it. This is known as gel blocking. Also, as SAP becomes more saturated, it swells and its volume increases. By confining the SAP in a small container of fixed volume it is possible to restrict the swelling of the SAP and prevent it from reaching its highest saturation levels (and by consequence stop the SAP from reaching its lowest levels of permeability). The degree to which the SAP particle is restricted depends on a number of factors, including: the nature and size of the container, the size and frequency of any breaks in the container (e.g., along the side walls), the amount of SAP disposed in the container, and the amount of fluid absorbed by the SAP. Further, the performance properties of SAP are affected by its degree of saturation. Specifically, absorbent composite properties such as permeability, absorption rate, capillary pressure (arising from the void space in the composite) will vary significantly as the SAP changes from dry to fully saturated. In accordance with a method of the present disclosure, target or optimal performance of the SAP may be achieved by changing the size of the container and/or the SAP concentration so as to physically constrain the swelling of the SAP and limit the maximum saturation point of the SAP. By incorporating these physical features, preferred levels of permeability or a preferred absorption property may be achieved in target regions of the absorbent core. Thus, by playing with the two variables of pocket size and the amount of SAP in the pocket, the minimum permeability of that container or pocket may be "set". Pockets in some regions of the diaper may be prevented from gel blocking and the permeability of that region of the core may be optimized. A gradient of pocket size may also be established to obtain maximum flow and utilization of the absorbent core. This gradient will be radiate from the target zone towards the ends or sides of the diaper.

The various arrangements of containers or pockets also promote SAP and core utilization and prevent fluid from bypassing the containers. Ideally, fluid should leak or flow from container to container as the SAP reaches the maximum level of saturation which is set either by the properties of the SAP or the volume of the pocket into which it is expanding. Applicants contemplate that, in some of the previously described composites or arrangements of pockets (see FIG. 6), there may be a tendency for fluid to leak between the pockets. That is the fluid runs along the channels formed by embossing lines and does not enter the core. To mitigate this tendency, arrangements or patterns for the containers are preferably ones that minimize or eliminate short and direct routes (as may be established along embossing lines) of fluid flow from the core center to the side margins of the core. Specifically, embossing lines for the fluid to flow along from the center of the core to the side edge of the core. To illustrate, containers or pockets shaped as diamonds are preferred to ones formed in squares or rectangles, because the diagonal lines or channels formed by the diamond containers are longer and more circuitous. Circles are also effective if packed in a way that does not present channels that flow quickly to the edge. In more preferred arrangements, fluid flow is forced to change directions one or more times before flowing through the side of the diaper.

An absorbent core for a baby diaper or adult incontinence product is required to absorb fluid quickly, in an anatomically aligned region of the core, absorb all the fluid without leaking at the sides or ends of the product and hold on to that fluid without wetting the user's skin particularly when under the pressure caused by the user's bodyweight. This present disclosure accomplishes that by providing regions of the core having different performance parameters defined by the size of the containers retaining the SAP, as well as the arrangement of the containers. Thus, a core may be designed to attain optimized performance characteristics by changing the size of the pocket and/or the concentration of SAP within that pocket.

In certain arrangements shown here, design features are combined to provide a core that is less likely to leak, absorbs wetness fast, and provides a dry, comfortable feeling for the user. At the crotch region of the core, the container size and SAP loading are optimized to provide an open structure, with high permeability, resulting in fast acquisition or distribution of fluid away from the point of insult and away from the user's skin. Permeability is maintained even when the SAP is swollen due to the physical constraints of the container restricting further swelling. This allows the liquid to spread more efficiently towards the regions further away from the target zone (crotch area), and contributes to better performance and utilization of the absorbent core. At regions away from the crotch region, such as regions proximate the periphery of the core and beyond, permeability is reduced to slow down the fluid. Absorption capacity is increased by the larger pockets allowing the SAP to swell more fully and hold on to more fluid.

In FIG. 15A, large diamond shaped containers or pockets 514 of absorbent particles aggregate 522 are present in a region anatomically aligned with the point of insult. The containers then gradually reduce in size toward the sides and front and rear margins or edges of the core 510. There are three distinct regions of containers. In the crotch region "A", large diamond shaped pockets are provided. Adjacent and surrounding the crotch region is an intermediate region "B" of pockets of smaller size than those in the crotch region (A). Among other things, the smaller pockets of this intermediate region (B) present breaks in the potential fluid flow around the SAP aggregates and along embossing lines. As described previously, the presentation of such barriers to direct escape of fluid flow through the side margins prevents leakage and promote utilization of the SAP aggregates. Finally, a third region "C" of pockets is present near each of the end edges of the core 510 populated by even smaller sized pockets of SAP aggregates.

FIG. 15B illustrates a second exemplary arrangements of SAP aggregates 522 and pockets 514. In this example, small, diamond shaped pockets 522 are disposed in the region anatomically aligned with the point of fluid insults. The pockets then gradually increase in size in regions disposed toward the sides and front and rear edges of the core. The two arrangements (in FIGS. 15A and 15B) provide alternative ways of structuring the expected flow gradient and as well, handling of the liquid insults. The absorbent composite and arrangement of pockets in FIG. 15A may provide for a center region with a larger capacity initially, but which, over time, will redistribute liquid in its void volume, or from subsequent liquid insults, to smaller adjacent pockets or cells. With the pattern of FIG. 15B, the center region may be equipped with smaller capacity initially, which will cause the liquid to travel to larger cells. It may also generate a surface topography that prevents leakage from the sides and ends of the diaper, i.e., "dams" will be created that intercept and absorb surface flow.

FIGS. 15C and 15D provide alternate arrangements wherein circular pockets for SAP aggregates are employed. In FIG. 15C, large, circular shaped pockets are present in a region anatomically aligned with the point of insult. The pockets 534 gradually reduce in size toward the sides and front and rear edges of the core 530. The pattern is similar to that employed in FIG. 15A but with circular pockets rather than diamond-shaped ones. Many of the characteristics of the arrangement in FIG. 15A translate to the design of FIG. 15C, however. Unlike a diamond shaped pocket, it is not possible to produce a perfectly close packed pattern with circular shaped pockets and the resulting space between the circular pockets could be disposed in a number of ways. It is envisaged that the space between the circular pockets could either be completely embossed (i.e., have large embossed, thermally bonded regions between the pockets), partially embossed or not embossed. The spaces could also contain SAP or be free of SAP.

FIG. 15D illustrates a further embodiment of the present invention, with a pattern analogous to that found in FIG. 15B. In this example, small, circular shaped pockets 544 are disposed in the region anatomically aligned with the point of fluid insults. The pockets 544 gradually increase in size in regions disposed towards the sides and front and rear edges of the core. Again the space between the pockets 544 could be utilized in a number of ways as described above.

It should be noted that arrangements and embossed patterns are not limited to employment of diamond shaped pockets or circular shaped pockets. Other shapes are contemplated. Some arrangements may even utilize different pocket shapes within the same pattern.

The following table summarizes the characteristics of the different pocket sizes, assuming the SAP concentration remains uniform throughout the core.

TABLE 1

Summary of Performance by Product Size and degree of SAP Saturation

| SAP Saturation | Small | Pocket Size Medium | Large |
|---|---|---|---|
| Dry (0%) | | Very high permeability Moderate absorption rate High capacity remaining | |
| Low (10-20%) | High permeability High absorption rate Low capacity remaining | High permeability High absorption rate Moderate capacity remaining | High permeability High absorption rate High capacity remaining |
| Medium (20-60%) | High permeability No further absorption | High permeability Low absorption rate Low capacity remaining | High permeability High absorption rate Moderate capacity remaining |
| High (60%+) | — | Moderate permeability No further absorption | Low permeability Low absorption rate Low capacity remaining |

Systems, Method, and Structures for Absorbent Particles Construction and/or Stabilization In a further variation of providing an absorbent composite according to the present disclosure, one or more of the nonwoven webs employed in previous examples is replaced with a more open structure. Examples of such a nonwoven include, carded PET webs, airthrough bonded nonwovens, resin bonded nonwovens and non-absorbent air-laid structures. Materials known as acquisition and distribution layers (ADL) are included in this list of suitable materials. The resulting structure provides an alternative means for containing absorbent particles and more specifically, within a fibrous network but without using an absorbent matrix of fibers (i.e., without pulp). The structure promotes the distribution of the SAP within a network of fibers provided by the non-woven web layer. This distribution of SAP particles into the more open web provides, among other things, a mechanism for further stabilization of the SAP within the nonwoven simply through entanglement of the particles within the fibrous network.

Figure 16A:
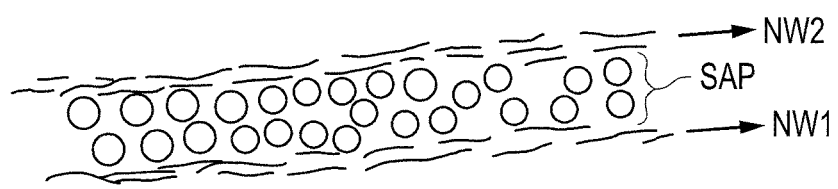
FIG. 16A is a simplified illustration of a prior art SAP sandwich.
Figure 16B:
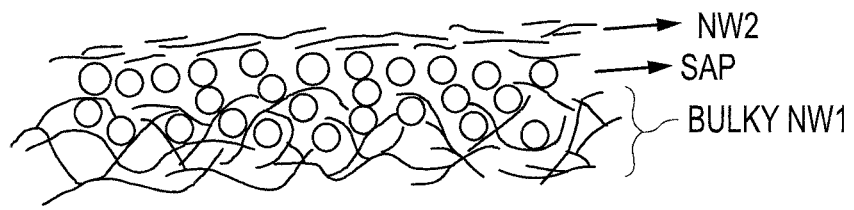
FIG. 16B is a simplified illustration of an SAP structure (sandwich) in accordance with the present disclosure.

FIG. 16 A illustrates a composite structure as previously described. The composite employs a non-woven as a bottom layer (NW1) and a top layer (NW2) to sandwich a layer of SAP material (SAP). FIG. 16B illustrates an alternative structure, wherein a bulky non-woven ("bulky" NW1) is employed as a base layer. The bulky non-woven layer NW1 provides fibers that extend outward and entangle SAP particles. Such entanglement with the fibers in the more open material leads to stabilization of the SAP within the absorbent composite. In a manufacturing process, SAP particles applied onto a sheet or web of the bulky woven may be energized so as to promote penetration into the fibrous network of the more open nonwoven web. The effect of gravity on the particles may be sufficient to promote the desired penetration as the SAP particles are laid down onto the web. Techniques such as vacuum or vibration could be used to further enhance the penetration of the SAP particles into the open, fibrous network.

Stabilization of the SAP prevents movement of the material during processing, storage and use. In exemplary embodiments, the absorbent composite or core may employ the "bulky noven" structure (as in FIG. 16B) for stabilizing the SAP in addition to the use of adhesive and containers or pockets of SAP aggregates, as previously described.

It should also be noted that the more open nonwoven material can provide additional performance features. These include faster acquisition of fluid and improved dryness (rewet) for the user. Also, the absorbent matrix will feel softer (spongier) than "flat" nonwoven webs, and will provide a more flexible composite. This results in greater comfort for the user and a better fit around the contours of the user's body leading to less chance of leakage.

Referring now to the illustrations in FIGS. 17A-17B, the exemplary absorbent composite is preferably provided with top layer of "bulky" nonwoven. The illustrations may be regarded as simplified cross-sectional views of the composite in FIG. 15A. Because the substrate used to contain the SAP is an open structure nonwoven, it is characterized by large pores (~2000 microns). Embossing will set and stabilize the local pore structure of the bulky, resilient fiber web substrate. Areas wherein the embossing pattern is small (utilizes small containers) (FIG. 17A) creates smaller pores (see FIG. 17A) compared to areas with larger embossing patterns (FIG. 17B) which creates larger capillary pores (17B). In other words, the smaller inter-fiber distance characterized by the smaller patterns lead to higher densities and higher capillarity. The larger patterns provide greater inter-fiber distances which lead to low density and low capillarity. The result of this combination of pockets across the core is an optimized wicking structure, as illustrated in FIG. 17C. With larger pores situated in the target area and smaller pores away from the insult point, an effective conduit for fluid flow results. This conduit may be utilized to transport liquid against gravity more efficiently. (See illustration of liquid movement in FIG. 17c). Such an advantageous structure can be created within the nonwoven substrate by the appropriate choice of embossing patterns hence allowing the liquid to spread further, enhancing core utilization and intake.

In further embodiments and in reference to FIGS. 17C and 17D, 3-D patterns or contours may be formed during use (uptake of liquid) as a consequence of SAP swelling. As shown in FIGS. 17C and 17D, different size pockets provide differences in swelling capacities, which in turn lead to differential swelling. In one respect, dams may be created by the pockets with greater swells (i.e., larger pillows). This structural consequence helps to reduce side and waist leakage. In most cases, uncontrolled liquid (liquid pooling on the surface of the product) lead to product leakage. The 3-D topography generated as SAP swells is defined by the embossing pattern size/frequency. An absorbent core that can self-generate a surface topography can inhibit cross-directional surface flow (to prevent side leakage) or discourage leakage at the waist region (longitudinal ends of the core). The structure and arrangement of pockets in FIG. 15A would be well suited to achieve these properties in an absorbent core.

Further Exemplary Methods and Systems for Making an Absorbent Composite Employing SAP.

In a method referred to as profiling, the SAP dosing rate is varied to produce a profiled core. See e.g., U.S. patent application Ser. No. 12/925,765 for profiled core designs, which document is incorporated by reference and made a part of the disclosure. The profiled core structure provides improved diaper performance by providing more absorbent material in areas of the core where it is needed. The profile may also be achieved by stacking multiple layers of the absorbent composite, but at different lengths (e.g., short top core, full length bottom core). A more efficient solution may be to vary the SAP dosing rate during application of the SAP and align the high SAP dose areas with the crotch area of the diaper when the core is converted in the diaper line. Such a method may be more efficient as it utilizes less nonwoven material than the stacked core. It is also cost effective.

In one embodiment, a powdered hotmelt adhesive is mixed with the SAP to provide additional bonding. The SAP and adhesive mixture is distributed between the two nonwoven webs and the hotmelt adhesive is "activated" by passing the composite through a heating device. Suitable devices include heated rollers, infra-red heater and the like. The adhesive melts and bonds the SAP and nonwovens together. This can also be combined with the patterned embossing/ultrasonic processes to produce pocket patterns as described previously. Typically, the adhesive/SAP is mixed at a ratio of 10 to 100 parts SAP to 1 part adhesive by weight (1-10% adhesive by weight). Too much adhesive will limit the absorption performance of the SAP, while too little adhesive may sacrifice structural integrity. Preferably, the adhesive is applied at a rate of about 1 to 2 particles of adhesive per particle of SAP. The exact rates may be worked out if the average particle size and density of the SAP and adhesive is known.

The absorbent composites described thus far are well suited for manufacturing in both offline and online manufacturing processes. In the offline process, the core machine stands separate to any other process and produces rolls, spools or boxes of festooned material that is then delivered to the diaper converting line. Typically, but not necessarily, the machine associated with the product of FIGS. 6-7, as described previously, would produce a wide sheet of the absorbent composite. The product is then slit to produce a number of rolls of material for use on the diaper converting line, e.g., a 1.5 m wide machine would produce 15 rolls of material at 100 mm width. In the offline process, the offline machine will typically run at speeds much slower than the diaper converting line. In the online process, the core machine is part of the diaper converting line and the core is made a part of the diaper converting process. The output speed of the core machine must match the speed of the diaper converting line and the width of the core will match the width of the core in the product.

Figure 18C:
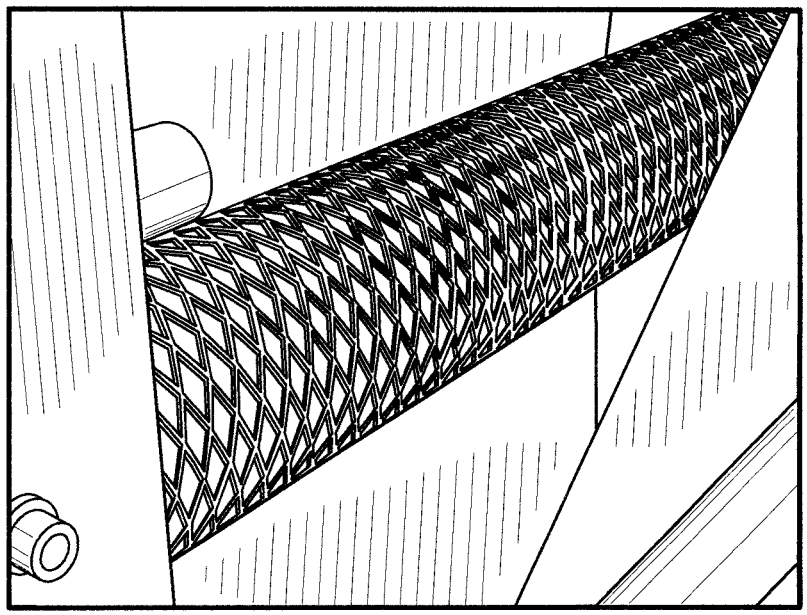

In an offline process depicted in FIG. 18A, an SAP sandwich is formed having a substrate A, a second substrate B and an SAP coating disposed between the two substrates. In one embodiment, the SAP is immobilized by bonding the two substrates together to contain the SAP in discrete planar volumes between the layers. One or a combination of the following methods for SAP stabilization may be employed. In a first process, heat embossing or ultrasonic bonding is employed to fuse the substrate layers in a defined pattern. In a second process, an adhesive is applied to one or both of the substrate inner surfaces. The two substrates are then strategically bonded together according to an advantageous embossing pattern. Thirdly, a thermal binder, such as low melting adhesive particles, may be mixed with the SAP particles. External heating is then applied to the composite to activate or melt the adhesive, thereby binding the particles to the substrate and to each other. Here, a patterned embossing step may be used to enhance the lamination quality while maintaining a more open SAP layer structure for enhanced liquid intake. If a patterned is not desired, a smooth calendar roll (not patterned), may also be employed to bond the cover layer to the SAP layer to produce the sandwich structure.

In an online process, the core forming process is directly coupled to the diaper converting process. The SAP sandwich structure is formed as with the first and second process discussed above, at speeds 3-4 times that of the offline process. The third method may not be suited to the faster online process because of the short dwell time required to heat and activate the thermal binder that is mixed in with the SAP. The offline process is designed to produce a wide material at slower speeds. The material output is then slit into narrower widths to supply several diaper lines. In contrast, the online process is designed to produce a narrow (1-wide) material at higher speeds and supply core material for only one diaper machine at a time.

So, in a preferred embodiment using the offline method according to the third method described above, a small quantity (10% or less) of hot melt particles is mixed in with the SAP. This particle mix is then uniformly deposited on substrate A, subjected to radiant IR heating to melt the adhesive particles. The second substrate B is then laid on top while the material is still hot. The layers are immediately laminated together using heat embossing with a patterned roll/smooth anvil embossing system. Table 2 below summarizes the process and provides certain parameters of a preferred embodiment.

TABLE 2

| | | Exemplary Offline Process of Manufacturing Using Hot Melt Adhesive | | | | |
|---|---|---|---|---|---|---|
| Core Structure | Substrate A | SAP BW, gsm | Hot Melt | Activation | Substrate B | Bonding Pattern |
| A | 20-80 gsm ADL web | 150-750 | Abifor 1605, 5-10% | IR Heating | Tissue | Diamond, 22 × 50 mm |

A coating line manufactured by Santex, Tobel, in Switzerland may provide the SAP scattering technology, IR heating and web handling. See e.g., FIG. 18B. The SAP material is chosen according to its suitability for the application, but in general, SAP with high retention capacity and high absorbency under load are preferred, for example, Centrifuge Retention Capacity (CRC) of from 20-40 g/g, a Pressure Absorbency Index (PAI) greater than 100 g/g An exemplary SAP is M-151 manufactured by Nippon Shokubai. A suitable hot melt adhesive is low melting EVA polymer, Abifor 1605, 0-200 micron particle size grade, which is currently available from Abifor Powder Technology, Switzerland. The bonding pattern specified for this embodiment is an elongated diamond with a major axis length of 50 mm oriented in the MD direction and a minor axis length of 22 mm. See e.g., FIG. 18C.

The present disclosure is, therefore, well adapted to carry out the objects and attain the ends and the advantages mentioned, as well as others inherent therein. While presently preferred embodiments (in the form of a diaper) have been described, numerous changes to the details of construction, arrangement of the article's parts or components, and the steps to the processes may be made. For example, the various topsheets, backsheet, absorbent core, containment walls and other absorbent composite structures may be utilized in other parts of the article or with other articles other than diapers. Such changes will readily suggest themselves of those skilled in the art and are encompassed within the spirit of invention and in the scope of the appended claims.

Although the present disclosure and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. An absorbent composite for incorporation into a disposable absorbent article, the absorbent composite comprising:
    a first fabric;
    a second fabric engaged with said first fabric at embossing sites such that a plurality of pockets are each defined by the first fabric being embossed with the second fabric at an embossing site; and
    a plurality of aggregates of absorbent particles, wherein each aggregate of absorbent particles is encircled by an embossing site and contained thereby within one of said pockets, wherein at least some of said pockets have fixed volumes and concentrations of absorbent particles therein such that said pockets physically restrict swelling of the absorbent particles therein and
    wherein the absorbent composite has a central crotch region, a pair of longitudinally spaced apart end edges and end regions, and a pair of laterally spaced apart side edges extending from end edge to end edge, the crotch region being located generally centrally between the side edges; and
    wherein multiple pockets of different volumes are arranged adjacent one another forming a gradient of higher volume pockets to lower volume pockets in an outwardly direction from the central crotch region toward the side edges or the end edges.

2. The absorbent composite of claim 1, wherein at least some of the pockets have fixed volumes and concentrations of absorbent particles therein such that the absorbent particles therein are prevented from gel blocking; and
    wherein said first is disposed generally flat and said second fabric is embossed therewith to form a domed cover over said first fabric and said SAP aggregate disposed therebetween.

3. The absorbent composite of claim 1, wherein the absorbent composite includes at least two different regions of pockets, including:
    a first region of pockets in a target, crotch zone of the absorbent composite that have a first fixed volume and a first concentration of absorbent particles therein; and
    a second region of pockets proximate a peripheral of the absorbent composite that have a second fixed volume and a second concentration of absorbent particles therein, wherein the first volume is different than the second volume, and wherein the first concentration is different than the second concentration.

4. The absorbent composite of claim 3, wherein the absorbent particles in the first region exhibit a higher permeability than the absorbent particles in the second region.

5. The absorbent composite of claim 3, wherein the first fixed volume is larger than the second fixed volume.

6. The absorbent composite of claim 3, wherein the second fixed volume is larger than the first fixed volume.

7. The absorbent composite of claim 3, wherein the absorbent composite includes a third region of pockets, the third region of pockets positioned between the first region and the second region, the third region of pockets having a third fixed volume and a third concentration of absorbent particles therein, wherein the third volume is different than the first and second volumes, and wherein the third concentration is different than the first and second concentrations.

8. The absorbent composite of claim 7, wherein the third fixed volume is smaller than the first fixed volume and larger than the second fixed volume.

9. The absorbent composite of claim 1, wherein pockets positioned adjacent other pockets share embossing sites with those other pockets.

10. The absorbent composite of claim 1, wherein each aggregate of absorbent particles is physically entrapped within one of said pockets such that said absorbent particles are maintained in place and stabilized within said pockets.

11. The absorbent composite of claim 1, wherein swelling of the absorbent particles is said pockets is restricted such that the absorbent particles are prevented from reaching a highest saturation level thereof.

12. The absorbent composite of claim 1, wherein swelling of the absorbent particles is said pockets is restricted such that the absorbent particles are prevented from reaching a lowest level of permeability thereof.

13. The absorbent composite of claim 1, wherein swelling of the absorbent particles is said pockets is restricted such that a maximum saturation point of the absorbent particles therein is limited.

14. The absorbent composite of claim 1, wherein the absorbent composite has a gradient distribution of pocket sizes.

15. The absorbent composite of claim 1, wherein the pockets have perimeters defined by embossing lines.

16. The absorbent composite of claim 15, wherein the embossing lines are oblique relative to edges of the absorbent composite.

17. The absorbent composite of claim 1, wherein the pockets include pockets having circle shaped perimeters.

18. The absorbent composite of claim 17, wherein spaces between the pockets are completely embossed.

19. The absorbent composite of claim 17, wherein spaces between the pockets are not embossed or are only partially embossed.

20. The absorbent composite of claim 17, wherein spaces between the pockets contain SAP.

21. The absorbent composite of claim 1, wherein the absorbent composite lacks and absorbent matrix of fibers.

22. The absorbent composite of claim 1, wherein the second fabric is engaged with said first fabric by discontinuous bond sites that encircle the SAP such that the pockets are only partially enclosed.

23. The absorbent composite of claim 1, wherein said first fabric is disposed generally flat and said second fabric is embossed therewith to form a cover over said first faric and said SAP aggregate disposed therebetween, and present domed cross section thereof.

24. An absorbent composite for incorporation into a disposable absorbent article, the absorbent composite comprising:
 a first fabric;
 a second, bodyside fabric embossed with said first fabric by a discontinuous embossing site such that a plurality of pockets are defined by the first fabric and the second fabric; and
 a plurality of aggregates of absorbent particles, wherein each aggregate of absorbent particles is within one of said pockets, wherein at least some of said pockets have fixed volumes and concentrations of absorbent particles therein such that said pockets physically restrict swelling of the absorbent particles therein;
 wherein the absorbent composite includes at least two different regions of pockets, including:
 a first region of pockets in a target, crotch zone of the absorbent composite that have a first fixed volume and a first concentration of absorbent particles therein; and
 a second region of pockets proximate a peripheral of the absorbent composite that have a second fixed volume and a second concentration of absorbent particles therein, wherein the first volume is different than the second volume, and wherein the first concentration is different than the second concentration;
 wherein the absorbent particles in the first region have a different swelling capacity than the absorbent particles in the second region; and
 wherein the first fabric in the first region exhibits a larger inter-fiber distance than an inter-fiber distance of the first fabric in the second region, such that the first region has a lower density and capillarity than the second region; and
 wherein each aggregate of absorbent particles is encircled by a discontinuous embossing site and contained thereby within one of said pockets, wherein at least some of said pockets have fixed volumes and concentrations of absorbent particles therein such that said pockets physically restrict swelling of the absorbent particles therein; and
 wherein said first fabric is disposed generally flat and said second fabric is embossed therewith to form a domed cover over said flat first fabric and said SAP aggregate disposed therebetween; and
 wherein the absorbent composite has a central crotch region, a pair of longitudinally spaced apart end edges and end regions, and a pair of laterally spaced apart side edges extending from end edge to end edge, the crotch region being located generally centrally between the side edges, said multiple pockets of different volumes being arranged adjacent one another and forming a gradient of higher volume pockets to lower volume pockets in an outwardly direction from the central crotch region toward the side edges and toward the end edges, and wherein pockets positioned adjacent other pockets share embossing sites with those other pockets.

25. A disposable absorbent article, comprising:
 a chassis body defined by a first end margin and a second end margin longitudinally spaced from the first end margin, the end margins partially defining front and back waist regions that are fastenable about a waist of a user;
 a topsheet;
 a backsheet, wherein the topsheet and backsheet define longitudinal and lateral margins of the chassis body; and
 an absorbent composite disposed between the topsheet and the backsheet, the absorbent composite comprising:
 a first fabric;
 a second, bodyside fabric engaged with said first fabric such that a plurality of domed pockets are defined by a flat first fabric and the domed second fabric; and
 a plurality of aggregates of absorbent particles, wherein each aggregate of absorbent particles is within one of said pockets, wherein at least some of said pockets have fixed volumes and concentrations of absorbent particles therein such that said pockets physically restrict swelling of the absorbent particles therein; and
 wherein each aggregate of absorbent particles is encircled by a discontinuous embossing line and contained thereby within one of said pockets, the discontinuous embossing line forming a perimeter of the domed cover between the domed cover and flat first fabric and wherein embossing lines are shared by more than one pocket.

* * * * *

UNITED STATES PATENT AND TRADEMARK OFFICE
CERTIFICATE OF CORRECTION

PATENT NO. : 11,426,311 B2
APPLICATION NO. : 16/538381
DATED : August 30, 2022
INVENTOR(S) : Andrew C. Wright and Eugenio G. Varona It is certified that error appears in the above-identified patent and that said Letters Patent is hereby corrected as shown below:

In the Specification

Column 7, Line 10, delete "an";
Column 7, Line 15, delete "discloses" and insert --disclosed--;
Column 9, Line 30, delete "inhibits" and insert --inhibit--;
Column 18, Line 13, delete "noven" and insert --nonwoven--;

In the Claims

Column 22, Line 34, insert --fabric-- after "first";
Column 23, Line 9, delete "is" and insert --in--;
Column 23, Line 13, delete "is" and insert --in--;
Column 23, Line 39, delete "and" and insert --an--.

Signed and Sealed this
Twenty-first Day of March, 2023

Katherine Kelly Vidal
*Director of the United States Patent and Trademark Office*